US012642754B2

(12) United States Patent
Cullen et al.

(10) Patent No.: US 12,642,754 B2
(45) Date of Patent: Jun. 2, 2026

(54) DISSOLVABLE HYDROGEN PEROXIDE TEETH WHITENING STRIP OR FILM

(71) Applicant: BSOLVE LIMITED, Glasgow (GB)

(72) Inventors: John Edward Cullen, Blantyre Glasgow (GB); Mark Alexander Livingstone, Blantyre Glasgow (GB); Melanie Macfarlane, Blantyre Glasgow (GB); Robert Crichton, Blantyre Glasgow (GB)

(73) Assignee: BSOLVE LIMITED, Glasgow (GB)

( * ) Notice: Subject to any disclaimer, the term of this patent is extended or adjusted under 35 U.S.C. 154(b) by 553 days.

(21) Appl. No.: 17/922,864

(22) PCT Filed: May 5, 2021

(86) PCT No.: PCT/GB2021/051087

§ 371 (c)(1),
(2) Date: Nov. 2, 2022

(87) PCT Pub. No.: WO2021/224618

PCT Pub. Date: Nov. 11, 2021

(65) Prior Publication Data

US 2023/0310284 A1     Oct. 5, 2023

(30) Foreign Application Priority Data

May 5, 2020     (GB) ..................................... 2006650

(51) Int. Cl.
| | |
|---|---|
| *A61K 8/22* | (2006.01) |
| *A61C 19/06* | (2006.01) |
| *A61K 8/02* | (2006.01) |
| *A61K 8/81* | (2006.01) |
| *A61Q 11/00* | (2006.01) |

(52) U.S. Cl.
CPC .............. *A61K 8/22* (2013.01); *A61C 19/066* (2013.01); *A61K 8/0208* (2013.01); *A61K 8/8147* (2013.01); *A61K 8/8176* (2013.01); *A61Q 11/00* (2013.01); *A61K 2800/57* (2013.01); *A61K 2800/92* (2013.01)

(58) Field of Classification Search
CPC ........ A61C 19/066; A61Q 11/00; A61K 8/22; A61K 8/0208; A61K 8/8147; A61K 8/8176; A61K 2800/57; A61K 2800/92
See application file for complete search history.

(56) References Cited

U.S. PATENT DOCUMENTS

| | | | |
|---|---|---|---|
| 6,458,380 B1 | 10/2002 | Leaderman | |
| 10,363,210 B2 | 7/2019 | Chopra et al. | |
| 2013/0101652 A1* | 4/2013 | Boyd ..................... | A61K 8/731 |
| | | | 424/401 |
| 2013/0266914 A1 | 10/2013 | Montgomery | |
| 2013/0287710 A1 | 10/2013 | Chopra et al. | |
| 2022/0226218 A1* | 7/2022 | Lees ................... | A61K 8/0245 |
| 2024/0050198 A1* | 2/2024 | Cullen ................. | A61K 8/8176 |

FOREIGN PATENT DOCUMENTS

| | | | | |
|---|---|---|---|---|
| CN | 1956696 | A | 5/2007 | |
| CN | 101163523 | A | 4/2008 | |
| CN | 103585027 | A | 2/2014 | |
| WO | 2012034127 | A1 | 3/2012 | |
| WO | WO-2013162404 | A1 * | 10/2013 | ........... A61K 6/0023 |

OTHER PUBLICATIONS

Chinese Office Action for corresponding Chinese Application No. 202180042488.2 dated Feb. 2, 2024.
International Search Report for PCT/GB2021/051087, mailed Sep. 30, 2021.

* cited by examiner

*Primary Examiner* — Sean M Basquill
(74) *Attorney, Agent, or Firm* — Barnes & Thornburg LLP

(57)     ABSTRACT

There is herein described a teeth whitening strip or film. In particular, the present invention relates to a dissolvable or substantially dissolvable hydrogen peroxide ($H_2O_2$) teeth whitening strip or film comprising a concentration of hydrogen peroxide ($H_2O_2$) at or above 10 wt. % of the strip or film. There is also described a process for the manufacture of a dissolvable or substantially dissolvable tooth whitening strip or film along with the method of using a strip or film comprising a concentration of hydrogen peroxide ($H_2O_2$) at or above 10 wt. % of the strip or film to whiten and/or bleach teeth.

23 Claims, 2 Drawing Sheets

DISSOLVABLE HYDROGEN PEROXIDE TEETH WHITENING STRIP OR FILM

CROSS REFERENCE TO RELATED APPLICATIONS

This application is a National Stage application of International Application No. PCT/GB2021/051087 filed May 5, 2021, which claims the benefit of and priority to GB2006650.2, filed May 5, 2020, the contents of which are incorporated herein by reference in their entirety.

FIELD OF THE INVENTION

The present invention relates to a teeth whitening strip or film. In particular, the present invention relates to a dissolvable or substantially dissolvable hydrogen peroxide ($H_2O_2$) teeth whitening strip or film comprising a concentration of hydrogen peroxide ($H_2O_2$) at or above about 10 wt. % of the strip or film. The present invention also relates to a process for the manufacture of a dissolvable or substantially dissolvable tooth whitening strip or film along with the method of using a strip or film comprising a concentration of hydrogen peroxide ($H_2O_2$) at or above about 10 wt. % of the strip or film to whiten and/or bleach teeth.

BACKGROUND

Human teeth naturally exhibit a variety of colours, which can be influenced by a number of factors, such as diet and/or medication. For instance, a number of foods, such as berries, and drinks, such as tea and red wine, contain chromogens which can stain teeth. Tobacco may also darken teeth. Other substances, such as acidic fruits and drinks, can promote staining by eroding dental enamel, softening teeth and making it easier for chromogens to attach. Consequently, there is a desire to whiten teeth to remove such staining.

It is known to use hydrogen peroxide ($H_2O_2$) to whiten teeth with relatively low concentrations of hydrogen peroxide ($H_2O_2$) between 6 wt. % and 7 wt. % of the strip or film.

However, a known problem is for the teeth whitening strip or film to remain dissolvable with higher concentrations of hydrogen peroxide ($H_2O_2$) such as at or above about 10 wt. % of the strip or film. It is therefore known that it is a problem in the art with the dissolution of whitening strips or films with high concentrations of hydrogen peroxide ($H_2O_2$).

It is an object of at least one aspect of the present invention to obviate or at least mitigate one or more of the aforementioned problems.

It is a further object of the present invention to provide a dissolvable or substantially dissolvable tooth whitening strip or film comprising hydrogen peroxide ($H_2O_2$) in a high-dosage form.

It is a yet further object of the present invention to provide a dissolvable or substantially dissolvable tooth whitening strip or film comprising hydrogen peroxide ($H_2O_2$) with the concentration of hydrogen peroxide ($H_2O_2$) at or above 10 wt. % of the strip or film.

It is a further object of the present invention to provide a process for manufacturing a dissolvable or substantially dissolvable strip or film with a concentration of hydrogen peroxide ($H_2O_2$) at or above 10 wt. % of the strip or film.

A yet further object of the present invention is to provide a cosmetic treatment for teeth whitening and/or teeth bleaching using a tooth whitening strip or film with a concentration of hydrogen peroxide ($H_2O_2$) at or above 10 wt. % of the strip or film.

SUMMARY OF INVENTION

According to a first aspect of the present invention there is provided a teeth whitening strip or film comprising:
  at least one or a combination of polyvinylpyrrolidone (PVP) polymers wherein the amount of the polyvinylpyrrolidone (PVP) polymers is greater than about 55 wt. % of the film or strip;
  an amount of at least about 10 wt. % hydrogen peroxide ($H_2O_2$); and
  at least one or a combination of polycarbophils.

The present invention therefore relates to providing a high dose of $H_2O_2$ in a thin dissolvable strip or film in a user's mouth which may be placed on teeth that has comparable residence/dissolution time to a lower dose film.

In the present invention, the polyvinylpyrrolidone (PVP) polymers may therefore be complexed with hydrogen peroxide ($H_2O_2$).

The hydrogen peroxide has been found to complex with the polymer (e.g. PVP), so an increase in the content of hydrogen peroxide ($H_2O_2$) in the formulation is accompanied by a significant increase in PVP/Polymer component.

The present invention therefore relates to a dissolvable or substantially dissolvable tooth whitening strip or film comprising hydrogen peroxide ($H_2O_2$) with the concentration of hydrogen peroxide ($H_2O_2$) at or above 10 wt. % of the strip or film.

The wt. % for all amounts recited herein is based on the wt. % of the film or strip.

The tooth whitening strips or films of the present invention may dissolve in a person's mouth in about 15-30 minutes. The tooth whitening strips or films may be placed onto a person's tooth or teeth and may therefore dissolve or substantially dissolve with the saliva in a person's mouth.

The hydrogen peroxide ($H_2O_2$) may be in a dry or substantially dry form in the film and/or may be formed in situ with a chemical reaction in the film when in contact with water such as saliva in the mouth.

The hydrogen peroxide ($H_2O_2$) may be sourced from any suitable source.

In particular, the hydrogen peroxide ($H_2O_2$) may be sourced and/or obtained from a polymer complex such as a polyvinyl complex.

In particular embodiments, the polymer complex may be PVP-$H_2O_2$. The polymer complex may be, for example, Peroxydone (Registered Trade Mark).

The polyvinyl complex may comprise: about 10-30 wt. % $H_2O_2$; about 10-25 wt. % $H_2O_2$; or about 16-20 wt. % $H_2O_2$. The wt. % is based on the wt. % of the dry film or strip.

The polyvinyl complex may comprise: about 70-90 wt. % PVP; about 75-90 wt. % PVP; or about 80-84 wt. % PVP. The wt. % is based on the wt. % of the dry film or strip.

Peroxydone (Registered Tarde Mark, Ashland Chemicals) contains about 16-20 wt. % $H_2O_2$ and about 80-84 wt. % PVP. The use of the PVP-$H_2O_2$ complex such as from Peroxydone (Registered Trade Mark, Ashland Chemicals) imparts greater stability of the peroxide during the drying process. Also, prior art from other companies exists on the use of PVP and $H_2O_2$ separately in gel form. There is the known problem of using Peroxydone (Registered Trade Mark, Ashland Chemicals) and that to obtain 10% $H_2O_2$ in the formula, where a large amount of the Peroxydone (Registered Trade Mark, Ashland Chemicals) is required, leaving little room for other components.

In the present invention, the polyvinylpyrrolidone (PVP) polymers may form a water soluble or substantially water-soluble, hydrogen bonded complex of linear or substantially linear polymer of n-vinylpyrrolidone (PVP). This may occur in a user's mouth such as on teeth being treated.

The polyvinylpyrrolidone (PVP) polymers may have a molecular weight of about 100,000-10,000,000 Daltons. In particular embodiments, the polyvinylpyrrolidone (PVP) polymers may have a molecular weight of: about 200,000-5,000,000 Daltons; about 500,000-10,000,000 Daltons; about 500,000-5,000,000 Daltons; about 1,000,000-1,700,000 Daltons or about 1,000,000-1,500,000 Daltons.

The hydrogen peroxide ($H_2O_2$) may be complexed with the n-vinylpyrrolidone in a mixture of: about 1:1 to about 1:3 molecular ratios; about 1:1 to about 1:2 molecular ratios; or about 1:1 or about 1:2 molecular ratios.

The hydrogen peroxide ($H_2O_2$) may be complexed with the vinylpyrrolidone (e.g. n-vinylpyrrolidone) or in a mixture to provide a concentration of hydrogen peroxide of any of the following: about 10-50 wt. %; about 10-40 wt. %; about 15-40 wt. %; about 20-40 wt. %; about 15-30 wt. %; about 15-25 wt. %; about 10-30 wt. %; or about 16-20 wt. %.

The tooth whitening film or strip is defined in terms of the dry weight of the film e.g. the weight of components dried to exclude water, expressed as percentages (i.e. wt. %) by total dry weight of the film alone i.e. without any backing sheet or support.

In particular embodiments, the polyvinylpyrrolidone (PVP) polymer used in the present invention may be Peroxydone K90 (Registered Trade Mark, Ashland Chemicals).

The present invention therefore provides a high dose of $H_2O_2$ in a thin dissolvable strip or film that has comparable residence/dissolution time to a lower dose film.

The present invention provides a dissolvable or substantially dissolvable teeth whitening strip or film comprising hydrogen peroxide ($H_2O_2$) with the concentration of hydrogen peroxide ($H_2O_2$) of: about 10 wt. % to 30 wt. % of the strip or film; about 15 wt. % to 30 wt. % of the strip or film; about 10 wt. % to 20 wt. % of the strip or film; or about 10 wt. % to 15 wt. % of the strip or film.

In the present invention there is use of polyvinylpyrrolidone (PVP) and/or n-polyvinylpyrrolidone (PVP) polymers in the strip or films. The amount of polyvinylpyrrolidone (PVP) and/or n-polyvinylpyrrolidone (PVP) polymers ranges from any of the following: greater than about 60 wt. %; about 60 wt. % to 99 wt. % of the strip or film; about 60 wt. % to 99 wt. % of the strip or film; about 65 wt. % to 95 wt. % of the strip or film; about 60 wt. % to 90 wt. % of the strip or film; about 65 wt. % to 95 wt. % of the strip or film; about 75 wt. % to 90 wt. % of the strip or film; or about 75 wt. % to 85 wt. % of the strip or film.

A particularly preferred polyvinylpyrrolidone (PVP) is Peroxydone K-90 (Registered Trade Mark, Ashland Chemicals). The Peroxydone K-90 is preferred as this is a complex of PVP and $H_2O_2$. The Peroxydone K-90 imparts greater stability of peroxide versus PVP and $H_2O_2$ separately. This is somewhat surprising as the Peroxydone is dissolved/dispersed in water during the mixing process and so suggests that the complex is either not completely destroyed or is reformed during the drying process.

The polyvinylpyrrolidone (PVP) may be a hygroscopic, amorphous polymer.

The polyvinylpyrrolidone (PVP) may be a linear non-ionic polymer that may be soluble in water and organic solvents and may typically be pH stable.

The polyvinylpyrrolidone (PVP) may also have adhesive and cohesive properties which may help in the formation of the strips and/or films of the present invention.

The increase in the level of Peroxydone has been found to allow a decrease in the level of other components previously used in the formation of strips or films used for teeth whitening.

To enable a higher concentration of $H_2O_2$, the level of polyvinylpyrrolidone (PVP) (e.g. Peroxydone) has to increase, therefore the level of the other components such as a second film former (e.g. pectin), which provides more extended dissolution, has to decrease. The inventors found that the level of polyvinylpyrrolidone (PVP) (e.g. Peroxydone) increased from about 61.5 wt. % to about 80 wt. % when moving from about 7 wt. % to 10 wt. % $H_2O_2$ composition and level of pectin decreased from about 25 wt. % to about 10 wt. %. Other components such as the plasticiser, emulsifier and flavours were also reduced to allow for more polyvinylpyrrolidone (PVP) (e.g. Peroxydone) and incorporation of the polycarbophil.

The present invention may also provide strips or films with decreased dissolution time. Increasing the level of the polyvinylpyrrolidone (PVP) (e.g. Peroxydone) increases the level of $H_2O_2$ and provides, for example, a consequent reduction in the level of pectin in the formulation. This significantly speeded up the dissolution of the formulation, which was undesirable as this would lead to a consequent reduction in adhesion time of the formula to the teeth and so reduction in whitening efficacy. The introduction of poly-carbophils (e.g. Noveon, Registered Trade Mark) at low amounts (e.g. about 1-5 wt. % or about 2-3 wt. %) allows for slowing of the dissolution rate of the composition and so likely increase in whitening efficacy.

The Noveon (Registered Trade Mark) may be Noveon AA-1 polycarbophil USP with a Brookfield viscosity of 2,000-12,000 (measured at Brookfield RVT, 20 rpm, neutralised to pH 7.3-7.8).

The polycarbophil may comprise the metal salt of polyacrylic acid cross-linked with a glycol.

In particular embodiments, the polycarbophil may comprise the calcium salt of polyacrylic acid cross-linked with divinyl glycol having a viscosity of, for example, between about 2,000-12,000 cP for about a 0.2% solution.

The polycarbophil may be in the form of the metal salt such as polycarbophil calcium. The polycarbophil may be formed as a synthetic polymer of polyacrylic acid cross-linked with divinyl glycol, with, for example, calcium as a counter-ion.

The increase of the PVP, such as Peroxydone K-90, increases the overall hydrogen peroxide ($H_2O_2$) content of the strips or films. Plasticiser may be used to ensure acceptable physical properties. Other ingredients such as flavour and taste may be chosen to ensure acceptable appearance and taste.

The present inventors have found that it is possible to prepare at least about 10 wt. % hydrogen peroxide teeth whitening strips or films that have a dissolution time that can be tailored to fit customer requirements.

Strips or films can be prepared that dissolve very quickly in the oral cavity, alternatively the inclusion of polycarbo-phils such as Noveon AA-1 affords strips or films that dissolve much less readily.

The polycarbophil may be in the form of a metal salt.

The teeth whitening strip or film my also comprise polyphosphates and/or hydroxy apatite.

The combination of "high" dose and slow dissolution is the basis for an improvement in the state of the art.

The present invention therefore relates to providing teeth whitening strips or films which comprise hydrogen peroxide (H₂O₂) at or above about 10 wt. % of the strip or film. The dissolution time of the strip or film may be tailored for a range of requirements. Strips or film may be prepared that dissolve very quickly in the oral cavity. Alternatively, components such as polycarbophils (e.g. Noveon AA-1) may be added to the strip or film to provide a longer dissolution time.

The hydrogen peroxide (H₂O₂) may therefore function as a bleaching agent to provide teeth whitening.

The teeth whitening strips or film may also comprise a range of other components including any one of or combination of the following:

one or more polyphosphates;
one or more hydroxyapatites;
one or more water soluble film-forming polymers;
one or more plasticizers; and/or
one or more emulsifiers.

The film or strip of the present invention may have a thickness ranging from: about 50 μm to about 500 μm; about 50 μm to about 250 μm; about 50 μm to about 100 μm; or about 100 μm to about 200 μm.

The soluble film-forming polymer may be one or more of the group comprising: polyvinyl pyrrolidone; pullulan; pectin; starch; dextrin; chitosan; alginic acid; salts of alginic acid and cellulose derivatives.

Suitable cellulose derivatives include carboxyalkyl cellulose or a salt thereof and hydroxyalkyl cellulose or a salt thereof, in which the alkyl group of the carboxyalkyl cellulose or the hydroxyalkyl cellulose is independently selected from C₁₋₅ alkyl, preferably methyl, ethyl or propyl. A preferred hydroxyalkyl cellulose may be hydroxypropyl cellulose.

Preferably, the water soluble film-forming polymer may be selected from the group comprising any one of or combination of the following: polyvinyl pyrrolidone; pullulan; pectin; starch; carboxyalkyl cellulose, or a salt thereof; hydroxyalkyl cellulose or a salt thereof, in which the alkyl group is independently selected from C₁₋₅ alkyl, alginic acid, salt of alginic acid, polyalkylene glycol in which the alkylene group has 2 or 3 carbon atoms and copolymers thereof, polyacrylic acid or a salt thereof and combinations thereof.

The water soluble film-forming polymer may be the polymer in a hydrogen peroxide-polymer complex which can form the dental bleaching agent. For instance, when the water soluble film-forming polymer is a polyvinyl pyrrolidone, it may be present in a complex with hydrogen peroxide as the dental bleaching agent.

The one or more film forming polymers may be present in the film or strip in a total amount of from: about 40% to about 95% by weight; about 50% to about 95% by weight; about 60% to about 95% by weight; about 50% to about 80% by weight; about 50% to about 70% by weight.

Preferably, the one or more film forming polymers may be present in a total amount of from about 50% to about 90% by weight. More preferably, the one or more film forming polymers may be present in a total amount of from about 60% to about 85% by weight. Still more preferably, the one or more film forming polymers may be present in a total amount of from about 65% to about 80% by weight.

In one embodiment, the one or more plasticizers may be selected from the group comprising a polyol such as glycerol, polyalkylene glycol, polyalkylene glycol monomethyl ether, monosaccharide, oligosaccharide, sorbital and sorbitan, in which the alkylene groups are independently selected from from C₁₋₅ alkylene, preferably methylene, ethylene or propylene. Preferred polyalkylene glycols may be one or both of polyethylene glycol and polypropylene glycol. A preferred polyalkylene glycol monomethyl ether may be polyethylene glycol monomethyl ether. A preferred plasticizer may be glycerol.

The one or plasticizers may be present in the film or strip in a total amount of from about 0.1% to about 15% by weight. Preferably, the one or plasticizers may be present in a total amount of from about 1% to about 12% by weight. More preferably, the one or plasticizers may be present in the film in a total amount of from about 3% to about 10% by weight.

The tooth whitening film may comprise one or more emulsifiers. In one embodiment, the one or more emulsifiers may be selected from ionic emulsifiers and non-ionic emulsifiers. In another embodiment the one or more emulsifiers may be selected from the group comprising a fatty acid derivative, a lecithin and a polysorbate.

Preferably the emulsifier, such as the non-ionic emulsifier, may be selected from the group comprising a saturated fatty acid derivative, a lecithin or a polysorbate. The fatty acids may be saturated or unsaturated. More preferably, the non-ionic emulsifier may comprise one or both of at least one unsaturated fatty acid such as oleic acid and/or linoleic acid and optionally at least one saturated fatty acid such as palmitic acid and/or stearic acid or a polysorbate.

More preferred emulsifiers, such as non-ionic emulsifiers, may be selected from fatty acids, which may be saturated or unsaturated and a polysorbate. More preferably the emulsifier, such as the non-ionic emulsifier, may comprise one or both of (i) at least one unsaturated fatty acid such as oleic acid and/or linoleic acid and optionally at least one saturated fatty acid such as palmitic acid and/or stearic acid and (ii) a polysorbate. A polysorbate may be a polyethoxylated ester of sorbital, sorbitan and isosorbide. Preferred saturated fatty acid derivatives include sucrose esters of saturated fatty acids; mono-, di- or tri-glycerides of saturated fatty acids; or sorbitan esters of saturated fatty acids.

The one or more emulsifiers may be present in the film in a total amount of from about 0.1% to 10% by weight. Preferably the one or more emulsifiers are present in a total amount of from about 0.2% to 5% by weight, more preferably from about 0.5% to 2% by weight.

In one embodiment, the tooth whitening film may further comprise water. The water may be present in the film in an amount of less than or equal to about 15% by weight, particularly from about 0.1% to 15% by weight. Typically, the tooth whitening film may further comprise water in an amount of from about 3% to 12% by weight, preferably from about 5% to 10% by weight.

In one embodiment, the tooth whitening film may further comprise one or more optional components selected from the group comprising colourant, gelling agent, flavouring, sweetener, acidifier, antioxidant and chelating agent.

The gelling agent may be a hydrocolloid adhesive agent.

Other components of the tooth whitening film, such as some types of water soluble film forming polymer like polyvinyl pyrrolidone and certain polysaccharides like hydroxypropyl cellulose may exhibit gelling. For the purpose of the present disclosure, when a gelling agent is present as an optional further component of the tooth whitening film, this is considered separately from, and in addition to any of the other components which may exhibit gelling behaviour.

The flavouring may be selected from the group comprising any one of or combination of the following: menthol; peppermint and an alkyl alkanoates, in which the alkyl group may be straight chained or branched and may comprise from 1 to 8 carbon atoms, and the alkanoate group may comprise from 1 to 5 carbon atoms.

The sweetener may be selected from one or more of the group comprising aspartame, acesulfame K, sucralose, cyclamate, erythritol, mannitol, sorbital, stevia and/or xylitol.

The acidifier may be phosphoric acid.

The antioxidant may be one or more selected from the group comprising tocopherol (vitamin E), tertiary-butylhydroquinone (TBHQ), butylated hydroxyanisole (BHA) butylated hydroxytoluene and ethylenediaminetetraacetic acid or a salt thereof.

The film or strip may comprise a chelating agent which may be ethylenediaminetetraacetic acid or a salt thereof. Chelating agents can be used to sequester heavy metal ions, thereby preventing the degradation of peroxy carboxylic acids.

In another embodiment, the tooth whitening film may be a single layer. In a further embodiment, the tooth whitening film is free of any other layer or layers such as barrier layers or supporting substrates.

In another embodiment, the film, which may be used without a dental aligner, may have a thickness in the range of from about 50 to 250 micrometers, more preferably the film has a thickness in the range of from about 100 to 200 micrometers, still more preferably about 150 micrometers.

Preferably, the film, which may be used without a dental aligner, has a length of from about 50 to 70 mm, more preferably about 60 mm. Preferably, the film has a width of from about 10 to 20 mm, more preferably about 15 mm.

The film, which may be used without a dental aligner, may have a weight in the range of from 80 to 250 mg, preferably from 130 to 200 mg, more preferably about 150 mg.

In another embodiment, the film, which may be used with a dental aligner, has a thickness in the range of from 50 to 150 micrometers, more preferably the film has a thickness in the range of from 60 to 130 micrometers, still more preferably about 70-125 micrometers.

In a second aspect, there is provided a process for the manufacture of a tooth whitening strip or film, the process comprising at least the steps of:

mixing at least one or a combination of polyvinylpyrrolidone (PVP) polymers wherein the amount of the polyvinylpyrrolidone (PVP) polymers is greater than about 55 wt. % of the film or strip; and an amount at least about 10 wt. % hydrogen peroxide ($H_2O_2$); and at least one or a combination of polycarbophils;

with water to provide an aqueous tooth whitening liquid;

applying the aqueous tooth whitening liquid to a substrate to provide a substrate carrying the aqueous tooth whitening liquid; and drying the aqueous tooth whitening liquid to provide a tooth whitening film on the substrate, said film having a thickness from about 50 μm to about 500 μm.

The tooth whitening strip or film may be as defined in the first aspect.

In one embodiment, the aqueous tooth whitening liquid comprises greater than 60 wt. % water (on the basis of the total weight of the tooth whitening liquid, which includes the water present), preferably from about 70 wt. % to 85 wt. % water. Thus, the aqueous tooth whitening liquid may comprise about 40 wt. % or less of the components forming the tooth whitening film, preferably from about 15 wt. % to 30 wt. %.

In one embodiment, the drying step comprises:

drying the aqueous tooth whitening liquid in air at a temperature of less than about 60° C.

In a further embodiment the drying of the aqueous tooth whitening liquid in air is carried out at a temperature in the range of from about 40° C. to less than 60° C., preferably from 40° C. to 55° C. In a further embodiment, the drying may be carried out at a rate in the range of from 0.2 to 2.0 m/min, preferably in a range of from 0.5 to 1.5 m/min, for instance by passing the aqueous tooth whitening liquid on the substrate through a dryer, such as a drying oven, hot air stream etc.

In a further embodiment, the drying step is carried out for a period of about 80 minutes or less, preferably for a period of about 35 minutes or less, more preferably for a period of about 25 minutes or less. The drying step may be carried out for a period of at least about 8 minutes, preferably for a period of at least about 15 minutes, more preferably for a period of at least about 20 minutes. Thus, the drying step may be carried out for a period of from about 8 to 80 minutes, preferably from about 15 to 35 minutes and more preferably from about 20 to 25 minutes.

In another embodiment, the mixing step may be carried out under high shear, for instance at a shear rate of greater than about 500 s$^{-1}$, preferably greater than about 1000 s$^{-1}$, up to a maximum of about 8000 s$^{-1}$. Preferably, the shear rate is in a range of from about 1000 s$^{-1}$ to 4000 s$^{-1}$.

In one embodiment, the mixing step further comprises mixing one or more further components selected from any one of or combination of the group comprising: colourant; gelling agent; flavouring; sweetener; acidifier; antioxidant and chelating agent.

In a third aspect, there is provided a tooth whitening strip or film obtainable by the process of the second aspect and its embodiments.

The formed strip or film and may be as defined in the first aspect or any other aspect described herein.

In a fourth aspect, there is provided a method of bleaching teeth, said method comprising at least the step of:

applying a tooth whitening strip film according to the first or third aspects to one or more teeth of a subject.

The method may be a cosmetic method, particularly a solely cosmetic method.

The film or strip may be applied to the front surface of one or more teeth and/or over the front surface of one or more teeth, chewing and/or back surfaces of one or more teeth.

Typically, the film or strips may be applied from a gum line of a user's mouth to the top of the teeth.

Typically, the treatment may be concluded when a user feels no residue and/or film remaining on the teeth.

According to a fifth aspect of the present invention there is provided a cosmetic method of bleaching teeth, said cosmetic method comprising at least the step of:

applying a tooth whitening strip or film according to any aspect of the present invention; and a dental aligner;

onto one or more teeth of a subject.

According to sixth aspect of the present invention there is provided a dental kit comprising a tooth whitening strip of film according to any aspect of the present invention and a dental aligner.

BRIEF DESCRIPTION OF THE FIGURES

Embodiments of the present invention will now be described, by way of example only, with reference to the following Figures.

DETAILED DESCRIPTION

Figure 1:
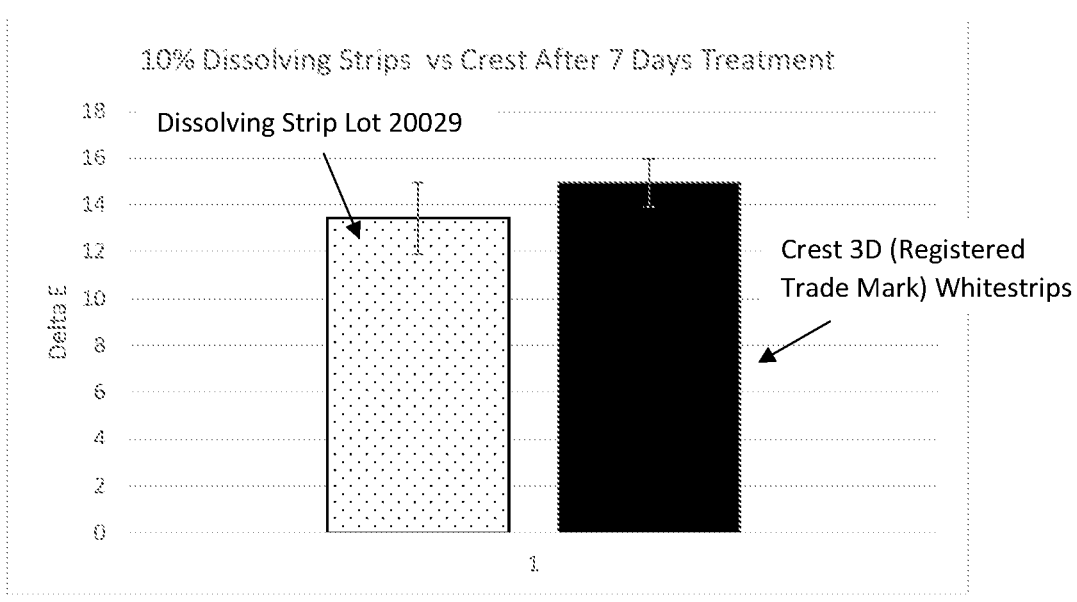
FIG. 1 shows 10 wt. % dissolving strips of Lot 20029 according to the present invention vs. Crest (Registered Trade Mark) according to the prior art after 7 days of treatment.

The present invention relates to a tooth whitening strip or film. In particular, the present invention relates to a dissolvable or substantially dissolvable hydrogen peroxide teeth whitening strip or film. The present invention also relates to a process for the manufacture of a dissolvable or substantially dissolvable tooth whitening strip or film along with the method of using said strip or film to whiten and/or bleach teeth.

The invention therefore provides a dissolvable or substantially dissolvable teeth whitening strip or film comprising hydrogen peroxide with the concentration of hydrogen peroxide ($H_2O_2$) at or above 10 wt. % of the strip or film.

It is widely known that it is difficult to provide a dissolvable or substantially dissolvable teeth whitening strip or film comprising hydrogen peroxide ($H_2O_2$) with the concentration of hydrogen peroxide ($H_2O_2$) at or above 10 wt. % of the strip or film.

The present invention provides a dissolvable or substantially dissolvable teeth whitening strip or film comprising hydrogen peroxide ($H_2O_2$) with the concentration of hydrogen peroxide ($H_2O_2$) of: about 10 wt. % to 30 wt. % of the strip or film; about 15 wt. % to 30 wt. % of the strip or film; about 10 wt. % to 20 wt. % of the strip or film; about 10 wt. % to 25 wt. % of the strip or film; or about 10 wt. % to 15 wt. % of the strip or film.

In the present invention there is use of polyvinylpyrrolidone (PVP) in the strip or films. The amount of polyvinylpyrrolidone (PVP) ranges from any of the following: greater than about 55 wt. % of the film or strip; greater than about 60 wt. % of the film or strip; about 55 wt. % to 99 wt. % of the strip or film about 55 wt. % to 99 wt. % of the strip or film; about 55 wt. % to 99 wt. % of the strip or film; about 60 wt. % to 99 wt. % of the strip or film; about 60 wt. % to 99 wt. % of the strip or film; about 60 wt. % to 99 wt. % of the strip or film; about 70 wt. % to 95 wt. % of the strip or film; about 70 wt. % to 90 wt. % of the strip or film; about 75 wt. % to 95 wt. % of the strip or film; about 75 wt. % to 90 wt. % of the strip or film; or about 75 wt. % to 85 wt. % of the strip or film.

A particularly preferred polyvinylpyrrolidone (PVP) is Peroxydone K-90 (Registered Tarde Mark, Ashland Chemicals).

The present invention may also provide strips or films with decreased dissolution time.

The increase of the PVP such as Peroxydone K-90 increases the overall hydrogen peroxide ($H_2O_2$) content of the strips or films. Plasticiser may be used to ensure acceptable physical properties. Other ingredients such as flavour and taste may be chosen to ensure acceptable appearance and taste.

It has also been found that the addition of additional components such as polycarbophils (e.g. Noveon) may be used to maintain a dissolution time for the strip or film. Noveon is a synthetic polymer of polyacrylic acid crosslinked with divinyl glycol.

The present applicant therefore prepares a strip or film comprising using a polyvinylpyrrolidone (PVP) such as Peroxydone as a polymeric source of hydrogen peroxide ($H_2O_2$).

The hydrogen peroxide is complexed with the polymer (e.g. PVP), so an increase in the content of hydrogen peroxide ($H_2O_2$) in the formulation is accompanied by a significant increase in PVP/Polymer component.

The advantage of using the hydrogen peroxide/PVP complex is that a higher percentage of hydrogen peroxide ($H_2O_2$) remains in the film post-manufacture than would be the case if the film were comprised of a formulation consisting of PVP and hydrogen peroxide added separately.

This appears to be due to a greater stability of the complexed composition versus the non-complexed composition when exposed to the drying process required to make thin films. In some situations, the increase in both HP and PVP may be desirable, but in others the increase in PVP may result in unexpected and undesirable properties of the final product.

In some situations, to achieve at least a 10 wt. % content of hydrogen peroxide ($H_2O_2$) there needs to be significant increase in polymer content, which is achieved by greatly reducing the content of other important formulation ingredients. Reduction on these other ingredients can impact important product parameters such as tensile strength, appearance, taste/aroma, and dissolution time.

The objective of the present invention is therefore to provide a dissolvable or substantially dissolvable tooth whitening strip or film that provides a high dose of hydrogen peroxide ($H_2O_2$) at or above 10 wt. % of the film or strip. The tooth whitening strip or film of the present invention therefore dissolves in a time frame comparable with a commercial product that has a lower dose of hydrogen peroxide ($H_2O_2$).

The present invention also provides a strip or film which provides a high dose of hydrogen peroxide ($H_2O_2$) at or above 10 wt. % of the film or strip which, on a twice a day basis gives comparable tooth residence time to a nondissolving whitening film of similar potency, whilst providing the improved convenience of not having to remove the film from the teeth post use. This addresses the previous problem of requiring improved whitening in reduced applications and therefore reduces the requirement for as many applications. Speed of teeth whitening shade change it is also improved using a high dose of hydrogen peroxide ($H_2O_2$) whitening strip or film.

Efficacy of teeth whitening strips is an effect of the combination of the strength of the whitening agent used and the contact time with the tooth. A high dose (>6 to 7 wt. %) hydrogen peroxide thin dissolvable strip has been prepared. Initially the high dose of $H_2O_2$ caused the resulting strips to have a vastly reduced dissolution time. The introduction of polycarbophil (e.g. Noveon AA-1) overcame the reduced dissolution time that was initially observed in first iterations. The present invention therefore provides a high dose of $H_2O_2$ in a thin dissolvable film or strip that has comparable residence/dissolution time to a lower dose film.

A fast dissolving/high dose dissolvable strip or film according to the present invention is advantageous and desirable in many situations such as teeth whitening.

There are high dose thin film products on the market, but these products do not dissolve completely and require the use of a backing liner, which needs to be eventually removed after application. There are other options such as dental trays that also offered, but these require the use of gels/liquids and lack the ease of use of application associated with the use of thin film strips.

A technical advantage of the strips or films according to the present invention is that by using a polymeric blend of PVP and $H_2O_2$ improves the stability of the $H_2O_2$ over and above the use of an $H_2O_2$ solution. This has been a surprising finding of the present invention.

The present inventors have been able to demonstrate a fast and slow dissolving film or strip, which both have at least a 10 wt. % $H_2O_2$ content. It may be demonstrated that there is control over the dissolution time.

To achieve a 10 wt. % $H_2O_2$ dose in a film or strip there is a requirement to increase the Peroxydone K-90 in the formulation. There are limits as to the total amount of Peroxydone K-90 that can be introduced to the formulation without detracting significantly from other properties of the films such as physical strength and processability in future manufacturing steps.

The introduction of polycarbophils (e.g. Noveon AA-1) into the formulation allows for high dose $H_2O_2$ whilst also ensuring there is no loss in dissolution time. An increase in Peroxydone K-90, and therefore the amount of PVP may be expected to increase the strength/toughness of the film, which could lead to brittleness and poor processability/user experience when delivered or further processed. The amount of plasticiser has been chosen to ensure suitable physical properties.

Addition of small percentage of Noveon AA-1 maintains a suitable dissolution time of the product.

The increase of Peroxydone K-90 also increases the overall $H_2O_2$ content of the films.

Plasticiser is used to ensure acceptable physical properties. Other ingredients such as flavour and taste are chosen to ensure acceptable appearance and taste.

All the constituent parts contribute together to ensure that a thin dissolvable strip or film where a high dose of $H_2O_2$ is prepared. The resulting dissolution time of the product can be tailored by further formulation to either be fast dissolving or alternatively if a longer residence time is desired this can be facilitated by use of other ingredients, such as Noveon AA-1. Increased Peroxydone requires reduction in level other components such as pectin which is the second film forming polymer that provides greater gelling and thus slowing of dissolution rate. Introduction of Noveon at, for example, about 2-3 wt. % level compensates for reduction in pectin and provides for slower dissolution.

Parameters such as physical thickness and dimensions of the film can determine properties such as dissolution time.

The tooth whitening strip or film may further comprise water. The water may be present in the film in an amount of less than about 15 wt. % by weight, particularly from about 0.1 wt. % to 15 wt. % by weight. Typically, the tooth whitening film may further comprise water in an amount of from about 3 wt. % to 12 wt. % by weight, preferably from about 5 wt. % to 10 wt. % by weight.

The tooth whitening film may further comprise one or more further components selected from any one of or combination of the group comprising: colourant; gelling agent; flavouring; sweetener; acidifier; antioxidant and chelating agent.

The tooth whitening film is defined in terms of the dry weight of the film i.e. the weight of components dried to exclude water, expressed as percentages (i.e. wt. %) by total dry weight of the film alone i.e. without any backing sheet or support.

The tooth whitening strip or film is flexible such that it is mouldable to, and can adopt the surface shape of the teeth.

The tooth whitening film comprises one or more water soluble film-forming polymers.

The water soluble film-forming polymer provides structure to the film and controls the release of the bleaching agent during tooth whitening. As used herein, a "water soluble" polymer is one in which one gram of polymer is soluble in 30 g or less of water. For instance, a polymer may be water soluble if 1 g of polymer is soluble in 25 g water.

The one or more water soluble film-forming polymers may be one or more selected from the group comprising: a polyvinyl pyrrolidone; polyacrylic acid or a salt thereof; polyalkylene glycol in which the alkylene group has 2 or 3 carbon atoms and copolymers thereof; and a polysaccharide.

Examples of polysaccharide water soluble film-forming polymers include any one of our combination of the following: pullulan; pectin; starch; dextrin; chitosan; alginic acid; salts of alginic acid and cellulose derivatives.

Suitable cellulose derivatives include any one of our combination of the following: carboxyalkyl cellulose or a salt thereof and hydroxyalkyl cellulose or a salt thereof, in which the alkyl group of the carboxyalkyl cellulose or the hydroxyalkyl cellulose is independently selected from $C_{1-5}$ alkyl, preferably methyl, ethyl or propyl. A preferred hydroxyalkyl cellulose is hydroxypropyl cellulose.

Preferably the water soluble film-forming polymer may be selected from the group comprising any one of or combination of the following: polyvinyl pyrrolidone; pullulan; pectin; starch; carboxyalkyl cellulose or a salt thereof; hydroxyalkyl cellulose or a salt thereof, in which the alkyl group is independently selected from $C_{1-5}$ alkyl, alginic acid, salt of alginic acid, polyalkylene glycol in which the alkylene group has 2 or 3 carbon atoms and copolymers thereof, polyacrylic acid or a salt thereof and combinations thereof.

More preferably, the water soluble film-forming polymer comprises a water soluble film-forming polymer selected from any one of or combination of the following: polyvinyl pyrrolidone; pullulan; pectin; starch; carboxyalkyl cellulose or a salt thereof; hydroxyalkyl cellulose or a salt thereof, in which the alkyl group is independently selected from $C_{1-5}$ alkyl, alginic acid; salt of alginic acid; polyethylene glycol; polypropylene glycol and copolymers of polyethylene glycol and polypropylene glycol; polyacrylic acid or a salt thereof.

The water soluble polymer may be selected from the group comprising any one of or combination of the following: polyvinyl pyrrolidone; hydroxylalkyl cellulose; hydroxyalkyl alkyl cellulose; carboxyalkyl cellulose; salts of carboxyalkyl cellulose; carbomer; dextrin; chitosan polyethylene glycol; polypropylene glycol and copolymers of polyethylene glycol and polypropylene glycol.

The polyvinyl pyrrolidone may be selected from any one of or combination of the following: uncrosslinked polyvinyl pyrrolidone; crosslinked polyvinyl pyrrolidone; a copolymer of vinyl pyrrolidone and acrylic acid; a copolymer of vinyl pyrrolidone and vinyl acrylate or alkylated polyvinyl pyrrolidone.

The polyvinyl pyrrolidone may preferably have a weight average molecular weight in the range of from 1 million to 1.5 million, still more preferably about 1.3 million.

The hydroxyalkyl cellulose may be one or both of hydroxyethyl cellulose and hydroxypropyl cellulose. With regard to the hydroxyalkyl alkyl cellulose, the hydroxyalkyl group may be independently selected from hydroxyethyl and hydroxypropyl while the alkyl cellulose may be independently selected from the group comprising methyl cellulose, ethyl cellulose and propyl cellulose. Preferably, the hydroxyalkyl cellulose is hydroxypropyl cellulose. Suitable hydroxypropyl cellulose is sold under the trade name Klucel (Registered Trade Mark) by Ashland.

The carboxyalkyl cellulose or a salt thereof many be carboxymethyl cellulose or an alkali metal salt thereof, such as sodium. Preferably the carboxyalkyl cellulose salt is sodium carboxymethyl cellulose.

Suitable sodium carboxymethyl cellulose is sold under the trade name Blanose (Registered Trade Mark) by Hercules Inc.

Typically, when the water soluble film-forming polymer is polyalkylene glycol in which the alkylene group has 2 or 3 carbon atoms or copolymers thereof, the polymer or copolymer should have a molecular weight of less than or equal to 200 000, particularly in the range of from 20,000 to 200,000.

Certain water soluble film-forming polymers may also function as adhesives, aiding attachment of the tooth whitening film to one or more teeth. Such adhesive water soluble film-forming polymers may be one or more selected from the group comprising a carboxyalkyl cellulose, a salt of carboxyalkyl cellulose, carbomer, dextrin, chitosan and polyethylene glycol. Polyethylene glycol, also known as polyethylene oxide, is a preferred adhesive water soluble film-forming polymer.

The one or more film forming polymers may be present in the film in a total amount of from about 40% to about 95% by weight. Preferably, the one or more film forming polymers may be present in a total amount of from about 60% to about 90% by weight. More preferably, the one or more film forming polymers may be present in a total amount of from about 70% to about 85% by weight. Still more preferably, the one or more film forming polymers may be present in a total amount of from about 75% to about 80% by weight.

Plasticizer

A plasticizer may be present in the tooth whitening film. Preferably the plasticizer should be a physiologically acceptable plasticizer.

The one or more plasticizers may be selected from the group comprising any one of or combination of the following: a polyol such as glycerol; polyalkylene glycol in which the alkylene groups are independently selected from from $C_{2-5}$ alkylene, polyalkylene glycol monomethyl ether in which the alkylene groups are independently selected from from $C_{2-5}$ alkylene, monosaccharide, oligosaccharide, sorbital and sorbitan, preferably ethylene or propylene. Preferred polyalkylene glycols are one or both of polyethylene glycol and polypropylene glycol. A preferred polyalkylene glycol monomethyl ether is polyethylene glycol monomethyl ether.

The plasticizer may be a hydrophilic plasticizer, such as one or more of the group comprising a polyol such as glycerol, polyethylene glycol, polyethylene glycol monomethyl ether, propylene glycol, sorbital and sorbitan. The preferred plasticizer is glycerol.

The one or plasticizers may be present in the film in a total amount of from about 0.1% to about 15% by weight.

Preferably the one or plasticizers may be present in a total amount of from about 1% to about 12% by weight. More preferably, the one or plasticizers may be present in the film in a total amount of from about 3% to about 10% by weight. When the dental bleaching agent comprises a non-hydrogen peroxide dental bleaching agent, such as PAP, the plasticizer may be present in a range of from 1 to 5% by weight. When the dental bleaching agent comprises hydrogen peroxide in a hydrogen peroxide-polymer complex, the plasticizer may be present in a range of from 8 to 12% by weight.

Emulsifier

The tooth whitening film comprises one or more emulsifiers. The one or more emulsifiers may be selected from ionic emulsifiers and non-ionic emulsifiers.

Preferably the non-ionic emulsifier is selected from the group comprising a saturated fatty acid derivative, a lecithin or a polysorbate. The fatty acids may be saturated or unsaturated. More preferably the non-ionic emulsifier comprises one or both of at least one unsaturated fatty acid such as oleic acid and/or linoleic acid and optionally at least one saturated fatty acid such as palmitic acid and/or stearic acid or a polysorbate.

Polysorbates are polyethoxylated esters of sorbital, sorbitans and isosorbide. Preferred saturated fatty acid derivatives include sucrose esters of saturated fatty acids; mono-, di- or tri-glycerides of saturated fatty acids; or sorbitan esters of saturated fatty acids. A preferred emulsifier is Sorbital, such as T80 supplied by Azelis.

The one or more emulsifiers may be present in the film in a total amount of from 0.1 to 10% by dry weight of the tooth whitening film, preferably in the range of from 2.0 to 2.5% by weight.

Optional Components

The tooth whitening film may further comprise one or more optional components selected from the group comprising any one of or combination of following: colourant, gelling agent, flavouring, sweetener, acidifier, antioxidant and chelating agent.

The gelling agent may be a hydrocolloid. Typically, the gelling agent may be a hydrocolloid which also functions as an adhesive agent. As used herein, the term "hydrocolloid" means a hydrophilic polymer, which may be of any origin such as plant, animal, microbial or synthetic, which contains hydrophobic groups and forms a gel in the presence of water, that is, a heterogeneous system with a solid hydrocolloid network containing a liquid water phase. The hydrocolloid adhesive agent may be selected from a natural gum, a polyacrylic acid or a poly alkylacrylic acid in which the alkyl group is methyl or ethyl. The alkyl group may be methyl or ethyl i.e. poly methacrylic acid or poly ethacrylic acid. The natural gum may be selected from alginic acid and its salts, agar, carrageenan, tragacanth and polysaccharide gums. More preferably, when the hydrocolloid gelling agent is a natural gum, it is tragacanth gum comprising a mixture of water-soluble and water-insoluble polymers, particularly polysaccharides, such as a mixture of tragacanthin and bassorin polymers. The bassorin polymer may be a polymer of fucose, xylose, arabinose, galacturonic acid and rhamnose.

Alternatively, the hydrocolloid adhesive agent may be a polymer of acrylic acid or an alkylacrylic acid as defined above. High molecular weight polyacrylic acid is also known as carbomer. Polymers of acrylic acid which may be either crosslinked or uncrosslinked. Examples of crosslinking agents include allyl ether pentaerythritol, allyl ethers of sucrose or ally ethers of propylene. Crosslinked polymers of acrylic acid are sold under the trade name Carbopol® by Lubrizol Corporation.

The polyacrylic acid may be provided as a salt, such as an ammonium, sodium, potassium, magnesium or calcium salt. Cross-linked polyacrylic acid, such as those cross-linked with divinyl glycol may be provided as salts such as magnesium or calcium salts, particularly calcium salts, also known as polycarbophils. Suitable polycarbophils are sold under the trade name Noveon™ by Lubrizol Corporation.

The gelling agent may be present in a range of from about 0.1 to 10% by dry weight of the tooth whitening film.

The flavouring may be an artificial flavouring or a natural flavouring. The flavouring may be selected from the group comprising menthol, peppermint and an alkyl alkanoate, in which the alkyl group may be straight chained or branched and may comprise from 1 to 8 carbon atoms, and the alkanoate group may comprise from 1 to 5 carbon atoms. Preferably the alkyl group of the alkyl alkanoate has 1, 2, 5 or 8 carbon atoms and the alkanoate group of the alkyl alkanoate may comprise from 1 to 5 carbon atoms, preferably 1, 4 or 5 carbon atoms. Preferred alkyl alkanoates are methyl butyrate [apple/pineapple], ethyl butyrate [orange/pineapple], iosamyl acetate [banana/pear], pentyl butyrate [pear/apricot], pentyl pentanoate [apple], octyl acetate [orange].

Peppermint is a common flavouring for tooth whitening films. Peppermint flavouring contains menthol as well as other components such as menthone, menthofuran, cineol, pulegone, together with some lesser ingredients.

Preferably the flavouring agent is present in a proportion of from 0.1 to 10 wt. % by dry weight of the tooth whitening film, more preferably from 1 to 5 wt. % by dry weight of the tooth whitening film.

The sweetener may be a sugar substitute, such as an artificial sugar substitute or a natural sugar substitute. An artificial sugar substitute may be one or more selected from the group comprising sucralose and cyclamate aspartame, advantame, saccharin, acesulfame potassium. A natural sugar substitute may be selected from the group comprising stevia, erythritol, mannitol, sorbital and xylitol. Preferably the sweetener is sucralose.

Preferably the sweetener is present in a proportion of from 0.01 to 5 wt. % by dry weight of the tooth whitening film. More preferably the acidifier is present in a proportion of from 0.05 to 0.5 wt. % by dry weight of the tooth whitening film.

The acidifier may be an inorganic acidifier or an organic acidifier. Phosphoric acid is a preferred inorganic acidifier. Preferred organic acidifiers are those selected from the group comprising lactic acid, malic acid, acetic acid, and citric acid, with citric acid being most preferred.

Preferably the acidifier is present in a proportion of from 0.1 to 5 wt. % by dry weight of the tooth whitening film. More preferably the acidifier is present in a proportion of from 1.0 to 1.5 wt. % by dry weight of the tooth whitening film.

The antioxidant may be one or more selected from tocopherol (vitamin E), tertiary-butylhydroquinone (TBHQ), butylated hydroxyanisole (BHA), butylated hydroxytoluene and ethylenediaminetetraacetic acid or a salt thereof. A preferred antioxidant is ethylenediaminetetraacetic acid (EDTA).

Preferably the antioxidant is present in a proportion of from 0.01 to 0.5 wt. % by weight of the tooth whitening film, more preferably from 0.05 to 0.15 wt. % by dry weight of the tooth whitening film.

The chelating agent may be ethylenediaminetetraacetic acid or a salt thereof. Chelating agents can be used to sequester heavy metal ions, thereby preventing the degradation of peroxy carboxylic acids.

The chelating agent may be present in an amount of from 0.1 to 5% by weight of the dry tooth whitening film.

A preservative may also be present in the tooth whitening film. Typical preservatives may be one or more compounds selected from the group comprising potassium sorbate, benzoic acid and its salts, propionic acid and its salts, salicylic acid and its salts and triclosan.

Preferably the preservative is present in a proportion of from about 0.01 to 5 wt. % by dry weight of the tooth whitening film. More preferably the preservative is present in a proportion of from 0.05 to 0.5 wt. % by dry weight of the tooth whitening film.

Also disclosed herein is a process for the manufacture of a tooth film. The film does not require the presence of further layers, such as barrier layers or supporting substrates.

The tooth whitening film is prepared from an aqueous tooth whitening liquid. The aqueous tooth whitening liquid is a mixture of the components of the tooth whitening film with water.

The hydrogen peroxide bleaching agent and water soluble film-forming polymer components of the tooth whitening film can be mixed with water to provide an aqueous tooth whitening liquid. The water is typically potable water. Distilled or de-ionised water may also be used. Preferably, the components are added to water under shear.

The mixing step may further comprise the addition of one or more further components of the aqueous tooth whitening film. The one or more further components may be selected from one or more of the group comprising colourant, gelling agent, flavouring, sweetener, acidifier, antioxidant and chelating agent.

The mixing parameters, such as shear force and duration, will be dependent upon the scale of the process of manufacture, as well as the component of the tooth whitening film to be mixed. This in turn will affect the choice of equipment to be employed in the mixing step.

Typically, the mixing step is initiated by adding any water soluble film-forming polymer and plasticizer into the water together with any optional gelling agent, further polymers or gums. Typically, any acidifier and any optional further components such as colourant, sweetener or other low level additives also will be added at this stage. The water soluble film-forming polymer and any other polymeric components or gums will be added in an order which prevents an early excessive viscosity build, i.e. the polymers or gums which produce the lowest viscosity build will be added first. Typically, any flavours will be mixed at the latter stages to prevent any degradation of thermally sensitive components or the loss of volatile components.

For example, the dental bleaching agent of hydrogen peroxide and polyvinyl pyrrolidone, can be mixed at a shear rate in the range of from 1000 to 6000 rpm. For smaller quantities on a laboratory scale, the shear rate may be in a range of from 2000 to 6000 rpm, preferably in a range of from 3000 to 4000 rpm. For larger quantities on an industrial scale, the shear rate may be in a range of from 1500 to 2500 rpm, preferably approximately 2000 rpm. The mixing time for smaller quantities on a laboratory scale can be in a range of from 5 to 20 minutes, preferably from 5 to 10 minutes. For larger quantities on an industrial scale, the mixing time may be in a range of from 10 to 20 minutes, preferably approximately 15 minutes.

Once the components are mixed with water to provide the aqueous tooth whitening liquid, it may be applied to a substrate. The aqueous tooth whitening liquid may be applied by known film-forming processes, such as dipping, spraying, knife over roller casting, extrusion and injection moulding.

A casting device may be used to apply the aqueous tooth whitening liquid to the substrate such as a caster, spreader, die or hopper. The aqueous liquid may be pumped into a spreader. If necessary, the temperature of the aqueous liquid may be held constant by heating elements in order to carefully control the viscosity of the liquid.

The spreader distributes the aqueous tooth whitening liquid homogeneously over a substrate and controls the thickness profile of the film. The spreader typically has a slot through which the aqueous tooth whitening liquid is cast. The slot is preferably designed to ensure that the hydrostatic pressure between the centre and the edges of the cast film is equilibrated. Preferably, the aqueous tooth whitening liquid is maintained at a constant temperature to ensure a constant viscosity and therefore homogenous thickness distribution of the resulting film.

Many different materials can be used for the substrate such as: copper; silver plated copper; chromium plated steel; stainless steel; metal coated with polyvinyl alcohol or gelatin; paper such as silicone coated paper; or polymer films such as polyethylene, polypropylene, polyester such as polyethylene terephthalate (PET), particularly siliconized PET, polytetrafluoroethylene (PTFE) films. Preferably the substrate comprises paper, paper coated with a release layer such as silicone, polyethylene, polypropylene, polytetrafluoroethylene (PTFE) or a polyester such as polyethylene terephthalate (PET), particularly siliconized PET films.

The aqueous tooth whitening liquid carried on the substrate can then be dried. Exemplary drying methods include indirect heating, heating by radiation and air stream drying.

In one embodiment, an air feed stream with no or a low moisture content is directed towards the aqueous tooth whitening liquid on the substrate and an air exhaust stream loaded with water vapour is removed. The air exhaust stream loaded with moisture may be vented or passed to condensers for the condensation and separation of liquid water.

It is possible to dry both surfaces of the aqueous tooth whitening liquid on the substrate. This can be achieved by looping the drying tooth whitening film around a series of polished rollers and directing air feed streams to each exposed surface in turn.

The air feed stream may be at ambient temperature. Alternatively, the air feed stream may be a heated air feed stream. Preferably, the heated air feed stream may have a temperature in the range of from greater than ambient to 60° C. More preferably, the heated air stream may have a temperature in the range of from 25° C. to 55° C., still more preferably in the range of from 45 to 55° C. The heating may be carried out in a belt heater with a belt speed in the range of from 0.2 to 2.0 m/min, and preferably at a speed in the range of from 0.5 to 1.5 m/min.

Alternatively, heated rollers or radiative heaters such as infra-red lamps may be used to dry the aqueous liquid to provide the film. These may heat the aqueous tooth whitening liquid carried on the substrate to a temperature in the range of from greater than ambient to 60° C., preferably to a temperature in the range of from 25° C. to 55° C.

The drying step may comprise first drying of a first surface of the aqueous tooth whitening liquid carried on the substrate to provide a first dried tooth whitening film carried on the substrate. The first surface of the aqueous tooth whitening liquid may be the outer surface of the liquid opposite to a second surface adjacent to the support. The first dried tooth whitening film may then be separated from the substrate. The second surface of the first dried tooth whitening film may then be second dried to provide a second dried tooth whitening film. The first and second drying may be independently carried out as discussed above.

In this way, a tooth whitening film can be provided which comprises less than 15% water by dry weight of the film. The water content is preferably in a range of from 3 to 12% by dry weight of the film, more preferably in a range of from 5 to 10% by dry weight of the film and even more preferably in a range of from 5 to 7% by dry weight of the film.

The tooth whitening film may be stored in sterile packaging, such as a sealed packet. The sealed packet may be water tight, and more preferably water and air tight. The packet may be made of a metallic foil such as aluminium foil, or a plastic film coated with a metallic layer.

The tooth whitening film obtainable by the method disclosed herein may be used in a method of bleaching teeth. The method may comprise at least the step of:

applying the tooth whitening film, obtained as described herein, to one or more teeth of a subject.

The method may be a cosmetic method. Preferably the method is a solely cosmetic method. As used herein, the term a "solely cosmetic method" means a cosmetic method which does not encompass the treatment or prevention of a medical condition or indication.

Certain aspects and embodiments of the invention will now be illustrated by way of example and with reference to the following tables.

EXAMPLES

The present invention may be exemplified as follows.

Example 1

Table 1 below shows the formulation of a teeth whitening strip according to the present invention wherein the strip comprises Peroxydone K-90.

TABLE 1

| DEV04705/19025-The basis for further supplemental formulations | | | | | | | |
|---|---|---|---|---|---|---|---|
| | | Ingredient dry weight (wt. %) | | | | | |
| Development number | Pectin | Peroxydone K-90 | Glycerol | Peppermint | Polysorbate 80 | Sucralose | Total |
| DEV04705 | 11.45 | 78.13 | 5.00 | 4.57 | 0.63 | 0.23 | 100.0 |

The dissolution time of the strips formed according to Table 1 were found to have a dissolution time of approximately seven minutes in the oral cavity. It was found that there was a desire to increase the dissolution time to a longer period of approximately 15 minutes as well as certain modifications to the physical appearance.

Example 2

DEV04856/DEV04863

The pectin in these formulations was increased to 13 wt. % and 12.76 wt. % from 11.45 wt. % by decreasing the concentration of peppermint flavour.

These formulations include for the first-time ingredients that impart a silver sparkle/lustre to the resulting strips.

Example 3

DEV04864/DEV04868

DEV04868 is a repeat of DEV04864.

Here pectin concentration has been slightly reduced from 11.45 wt. % to 11.20 wt. %.

The formulation includes Noveon AA-1 (2 wt. %), a high molecular weight acrylic acid polymer, which can provide controlled release characteristics in oral drug delivery applications.

Samples of DEV04868 found to dissolve almost twice as slowly as the samples from DEV04705/19025. This increase in oral cavity dissolution time was desirable.

Dissolution time was tested in-vitro using artificial saliva. The time taken for strips to dissolve in artificial saliva at 37° C. was recorded from strips from 19025 and DEV04868.

Results from testing of both samples are presented in Table 2.

TABLE 2

Comparison of average strip weight and dissolution time between 19025/DEV04705 and DEV04868 (average of three samples).

| Sample ID | Average strip weight (mg) | Average dissolution time (MM:SS) |
|---|---|---|
| DEV04705/19025 | 127.6 | 02:49 |
| DEV04868 | 152.2 | 07:59 |

It can be observed from Table 2 that the samples from DEV04868 were approximately 25 mg heavier than samples from 19025. DEV04868 samples exhibit an extended dissolution time over samples from 19025. No comparison between strips of comparable weights is available at this time, but it is unlikely that a sample of 19025 weighing approximately 150 mg would have a dissolution time comparable with DEV04868 samples.

Example 4

DEV04871

This formulation removes completely the pectin component of the formulation.

There is an increase in Peroxydone K-90 (88.70 wt. %) and there was for the first time added plasdone S-630.

The inclusion of plasdone was intended to provide strips with improved dissolution profile whilst also allowing for increase in Peroxydone and therefore $H_2O_2$ content. The removal of pectin had a detrimental effect on dissolution time with strips dissolving in oral cavity within 5 minutes. Based on the reduced dissolution time no further work was carried out with Plasdone S-630.

Example 5

DEV04874 and DEV04875 Comparison

DEV04874 included pectin at a slightly increased content (12.90 wt. %).

The Peroxydone K-90 was also slightly increased (80 wt. %). The slight increase of these ingredients was achieved by a reduction in the flavour component of the formulation (1.10 wt. %). There was no inclusion of additional ingredients such as Noveon or Plasdone, and therefore this formulation represents a close analogue of DEV04705/19025.

DEV04875 represents a modified version of DEV04705. The inclusion of 3 wt. % of Noveon at the expense of pectin was introduced here. The Peroxydone content was held at 80% wt. and there was a very slight reduction in peppermint flavour (1.00%). A comparison of dissolution time in-vitro and in-vivo was attempted. The results from dissolution testing are presented in Table 3.

TABLE 3

Comparison of dissolution time between DEV04875 and DEV04874.

| Development Number | Average sample weight (mg) | Dissolution Time (average) (MM:SS) | |
|---|---|---|---|
| | | In-vitro | In-vivo |
| DEV04875 | 139.4 | 07:13 | 21:26 |
| DEV04874 | 160.3 | 05:52 | 18:29 |
| Difference | 20.9 | 01:21 | 02:57 |

(MM:SS, is minutes and seconds for the dissolution to occur.)

DEV04874 represents a significant improvement on DEV04705. The in-vitro dissolution time has been increased by approximately 3 minutes.

DEV04875 despite being lower in strip weight has a dissolution time that exceeds that of DEV04874, and therefore indicates the importance of the inclusion of Noveon AA-1. Difference in dissolution time between DEV04874 and DEV04875 is even more impressive when difference in strip weight is taken into consideration. Based on the results disclosed here DEV04875 was the formulation taken to scale-up (Batch number 20009).

Batch 20009 was prepared and represented an improvement of processability over 19025. The solids content of batch 20009 was 27 wt. %.

The viscosity and processability of the casting liquid at this solids content were acceptable, but was very difficult to deaerate, which resulted in a final film that had an undesirable bubbled appearance. Batches DEV04887-DEV04889 were repeats of DEV04875 at reduced solids contents with the reduction of solids content aiding the process of degassing of casting liquid.

Others

DEV04876 was a formulation that included an ingredient (hydroxy apatite) that is known to have desensitising properties. The rationale for the inclusion of the hydroxy apatite was that the desensitising properties may offset any sensitivity that could be caused by regular use of a high strength hydrogen peroxide product. The inclusion of the hydroxyapatite was not detrimental to the formation of a film and could be another potential teeth whitening product. DEV04877 was a batch were the glycerol was substituted for sorbitol (Neosorb P60). There were no major issues encountered when swapping the plasticisers used in batch DEV04877.

Formulation Comparison

Please see Table 4 for a breakdown of ingredients and their dry weight percentages used in the batches discussed in this document.

TABLE 4

Raw materials and their loading used in formulations designed for 10% hydrogen peroxide teeth whitening strips.

| Development number | Pectin | Peroxydone K-90 | Glycerol | Peppermint | Poly-sorbate 80 | Sucralose | Noveon AA1 | Neosorb P60 | Hydroxy-apatite | Plasdone S630 | Silver Sparkle/Lustre | Total (%) |
|---|---|---|---|---|---|---|---|---|---|---|---|---|
| | | | | | | Ingredient dry weight (wt. %) | | | | | | |
| DEV04705 | 11.45 | 78.13 | 5.00 | 4.57 | 0.63 | 0.23 | 0.00 | 0.00 | 0.00 | 0.00 | 0.00 | 100.0 |
| DEV04856 | 13.00 | 78.00 | 5.00 | 2.60 | 0.60 | 0.00 | 0.00 | 0.00 | 0.00 | 0.00 | 0.80 | 100.0 |
| DEV04863 | 12.76 | 78.00 | 5.00 | 2.55 | 0.59 | 0.30 | 0.00 | 0.00 | 0.00 | 0.00 | 0.80 | 100.0 |
| DEV04864 | 11.20 | 78.00 | 5.00 | 2.20 | 0.50 | 0.30 | 2.00 | 0.00 | 0.00 | 0.00 | 0.80 | 100.0 |
| DEV04868 | 11.20 | 78.00 | 5.00 | 2.20 | 0.50 | 0.30 | 2.00 | 0.00 | 0.00 | 0.00 | 0.80 | 100.0 |
| DEV04871 | 0.00 | 88.70 | 4.00 | 1.00 | 0.00 | 0.30 | 0.00 | 0.00 | 0.00 | 5.00 | 1.00 | 100.0 |
| DEV04874 | 12.90 | 80.00 | 5.00 | 1.10 | 0.60 | 0.40 | 0.00 | 0.00 | 0.00 | 0.00 | 0.00 | 100.0 |
| DEV04875 | 10.00 | 80.00 | 5.00 | 1.00 | 0.60 | 0.40 | 3.00 | 0.00 | 0.00 | 0.00 | 0.00 | 100.0 |
| DEV04876 | 10.00 | 80.00 | 5.00 | 1.00 | 0.60 | 0.40 | 0.00 | 0.00 | 3.00 | 0.00 | 0.00 | 100.0 |
| DEV04877 | 12.90 | 80.00 | 0.00 | 1.10 | 0.60 | 0.40 | 0.00 | 5.00 | 0.00 | 0.00 | 0.00 | 100.0 |
| DEV04887 | 10.00 | 80.00 | 5.00 | 1.00 | 0.60 | 0.40 | 3.00 | 0.00 | 0.00 | 0.00 | 0.00 | 100.0 |
| DEV04888 | 10.00 | 80.00 | 5.00 | 1.00 | 0.60 | 0.40 | 3.00 | 0.00 | 0.00 | 0.00 | 0.00 | 100.0 |
| DEV04889 | 10.00 | 80.00 | 5.00 | 1.00 | 0.60 | 0.40 | 3.00 | 0.00 | 0.00 | 0.00 | 0.00 | 100.0 |

Example 6

Thin films (Batch Number DEV04150) containing Peroxydone were manufactured by mixing 13.5 g pectin (CP Kelco), 37.88 g Peroxydone K-90 (ISP/Ashland), 4.29 g glycerol (Brenntag), 2.51 g peppermint (Givaudan), 0.89 g Tween 80 (Sigma), 0.12 g sucralose (Tate & Lyle) and 220.8 g of water (VWR) using an Ultra-turrax UT-50 high-shear mixer. Aliquots of the mixture were then degassed and cast at a knife height setting of 850 microns onto silicone coated paper using a Sheen 1133N film coater (Sheen Instruments). The films were air dried at a temperature of less than 40° C. for 35 minutes.

Thin films (Batch Number DEV04151) containing a combination of hydrogen peroxide and PVP were manufactured by mixing 13.5 g pectin (CP Kelco), 31.06 g Kollidon 90 (BASF Luviskol), 19.48 g of 35 wt. % hydrogen peroxide of 850 microns onto silicone coated paper using a Sheen 1133N film coater. The films were air dried at a temperature of less than 40° C. for 35 minutes.

The casting liquid used and samples of the films after 25 and 35 minutes drying were analysed for hydrogen peroxide content. For the casting liquid a quantity of equivalent weight to that used to produce 10 dried films of dimension 2 cm×6 cm was calculated using the theoretical solids content of the batches and weighed out, dissolved in water and titrated with potassium permanganate to determine the hydrogen peroxide content. For the dried films an area of material equivalent to that of 10 dried films of 2 cm×6 cm was dissolved in water and titrated with potassium permanganate.

TABLE 5

Dental bleaching compositions

| Drying Time (mins) | Quantity Material Weighed (mg) | Quantity Potassium Permanganate Required for Titration (ml) | Calculated Quantity of Hydrogen Peroxide (mg) | Theoretical Dry Weight of Film (mg) | Hydrogen Peroxide in Theoretical Dry Film Weight (wt. %) | wt. % of Initial Hydrogen Peroxide |
|---|---|---|---|---|---|---|
| | | DEV04150 (Peroxydone containing films) | | | | |
| 0 (casting liquid) | 6970 | 79.34 | 135.0 | 1474 | 9.16 | 100.0 |
| 25 | 2095 | 75.47 | 128.4 | 1470 | 8.73 | 95.3 |
| 35 | 1470 | 63.24 | 107.6 | 1470 | 7.32 | 79.9 |
| | | DEV04151 (PVP and Hydrogen Peroxide Solution containing films) | | | | |
| 0 (casting liquid) | 6920 | 99.43 | 169.1 | 1400 | 12.08 | 100.0 |
| 25 | 1786 | 85.23 | 145.0 | 1433 | 10.12 | 83.8 |
| 35 | 1433 | 65.62 | 111.6 | 1433 | 7.79 | 64.5 | solution (Univar), 4.29 g glycerol (Brenntag), 2.51 g peppermint (Givaudan), 0.89 g Tween 80 (Sigma), 0.12 g sucralose (Tate & Lyle) and 220.84 g of water (VWR) using an Ultra-turrax UT-50 high-shear mixer. Aliquots of the mixture were then degassed and cast at a knife height setting From the results it can be seen that the films containing Peroxydone retain a significantly greater percentage of the initial quantity of hydrogen peroxide assayed following the drying process in comparison to films made using PVP and hydrogen peroxide solution.

These results suggest that the aqueous film processing utilised has surprisingly preserved the stabilising properties of Peroxydone K-90 despite the material being dissolved in water during the manufacturing process.

Results and Discussion

From the results it can be seen that the films containing Peroxydone retain a significantly greater percentage of the initial quantity of hydrogen peroxide assayed following the drying process in comparison to films made using PVP and hydrogen peroxide solution. These results suggest that the aqueous film processing utilised has surprisingly preserved the stabilising properties of Peroxydone K90 despite the material being dissolved in water during the manufacturing process.

Consequently, use of the process described herein provides a tooth whitening film of increased potency, the film having a higher concentration of hydrogen peroxide bleaching agent compared to other aqueous based processes in which a similar concentration of free hydrogen peroxide is added to the aqueous tooth whitening composition.

Example 7

We also attach an example below which compares the percentage composition of the 7 wt. % and 10 wt. % hydrogen peroxide formulations to illustrate the changes in the composition that have been needed to achieve the higher peroxide level whilst maintaining the dissolution time.

Teeth Whitening Formulations

| Ingredient | 7% Peroxide Formula % | 10% Peroxide Formula % |
|---|---|---|
| Peroxydone K90 | 61.5 | 80.0 |
| Pectin | 25.3 | 10.0 |
| Glycerol | 7.0 | 5.0 |
| Peppermint Flavour | 4.5 | 1.0 |
| Tween 80 | 1.5 | 0.6 |
| Sucralose | 0.2 | 0.4 |
| Noveon AA-1 | 0.0 | 3.0 |
| Total | 100.0 | 100.0 |

Example 8

DEV04939—10% Hydrogen Peroxide+Phosphates

DEV04939 is the first development sample prepared that was designed to have both a high level of $H_2O_2$ and the inclusion of both sodium hexametaphosphate (SHMP) and sodium tripolyphosphate (STPP). The inclusion of both phosphates has been demonstrated to have beneficial effects on whitening efficacy. It is the case that including both phosphates at a total loading was achieved by reducing the percentage of peroxydone included in the formulation. The measured level of hydrogen peroxide is presented alongside assay results for a non-phosphate containing analogue (DEV04938) in Table 6.

TABLE 6

Comparison of $H_2O_2$ assay results for a whitening strip that contains phosphates (DEV04939) against a non-phosphate analogue (DEV04938).

| Sample ID | Weight (mg) | $H_2O_2$ (wt. %) in strip | Sample ID | Weight (mg) | $H_2O_2$ (wt. %) in strip |
|---|---|---|---|---|---|
| DEV04938.1 | 148.0 | 9.62 | DEV04939.1 | 121.3 | 8.18 |
| DEV04938.2 | 145.1 | 9.21 | DEV04939.2 | 122.3 | 8.30 |
| DEV04938.3 | 125.4 | 9.55 | DEV04939.3 | 134.9 | 9.15 |
| DEV04938.4 | 134.9 | 8.95 | DEV04939.4 | 117.0 | 8.17 |
| DEV04938.5 | 137.9 | 9.00 | DEV04939.5 | 130.9 | 8.19 |
| Average | 138.3 | 9.27 | Average | 125.3 | 8.40 |

It can be observed that reducing the level of peroxydone has the effect of reducing the ultimate level of $H_2O_2$ present in the strips. Despite the lower level of hydrogen peroxide in the phosphate containing formulation it was found that in an internal in-vitro whitening study that the phosphate containing strip out-performed the non-phosphate containing analogue (Table 7).

TABLE 7

Whitening results for development batches DEV04938/9

| Sample ID | Δ E[1] | $H_2O_2$ assay |
|---|---|---|
| DEV04939 | 34.0 | 9.16 wt. %[2]/8.40 wt. % |
| DEV04938 | 28.2 | 9.40 wt. %[2]/9.27 wt. % |

[1]ΔE—represents the overall colour change of test substrates. A higher value indicates a larger shift from starting point (stained test substrate) to lighter/whiter test substrate.

[2]Samples of strips from the batch were assayed prior to starting whitening study, these results are presented alongside previous assay results from Table 6

Despite a lower overall percentage of $H_2O_2$ the phosphate containing formulation has resulted in improved whitening, but both strips will have very fast dissolution times, which may be undesirable.

Therefore, it is advantageous to develop a whitening strip that contains both phosphates and has an extended dissolution time. Additionally, to include other ingredients in the formulation that provide other benefits to the user then this would also be deemed as beneficial.

Table 8 summarises development batches that have been prepared to investigate possibility of the preparation of a dissolving strip that has the following features:

Extended dissolution time

High $H_2O_2$ content

Capable of holding other ingredients (phosphates and hydroxyapatite)

TABLE 8

Summary of development samples prepared to prepare a dissolving whitening
strip that has both phosphates present as well as an extended dissolution time.

| | Ingredient dry weight (w/w %) | | | | | | | | | | |
| Development/ Batch number | Pectin | Peroxy- done K-90 | Glycerol | Pepper- mint | Poly- sorbate 80 | Sucralose | Noveon AA1 | Hydroxy- apatite | SHMP | STPP | Total (%) |
|---|---|---|---|---|---|---|---|---|---|---|---|
| DEV04938 | 12.9 | 80.0 | 5.0 | 1.1 | 0.6 | 0.4 | | | | | 100.0 |
| DEV04939 | 12.9 | 73.0 | 5.0 | 1.1 | 0.6 | 0.4 | | | 3.5 | 3.5 | 100.0 |
| DEV04964 | 12.9 | 73.0 | 5.0 | 1.1 | 0.6 | 0.4 | | | 3.5 | 3.5 | 100.0 |
| DEV04965 | 10.9 | 73.0 | 5.0 | 1.1 | 0.6 | 0.4 | 2.0 | | 3.5 | 3.5 | 100.0 |
| DEV04966 | 8.9 | 73.0 | 5.0 | 1.1 | 0.6 | 0.4 | 4.0 | | 3.5 | 3.5 | 100.0 |
| DEV04969 | 12.9 | 71.0 | 5.0 | 1.1 | 0.6 | 0.4 | | 2.0 | 3.5 | 3.5 | 100.0 |
| DEV04970 | 9.9 | 71.0 | 5.0 | 1.1 | 0.6 | 0.4 | | 5.0 | 3.5 | 3.5 | 100.0 |
| DEV04971 | 9.9 | 71.0 | 5.0 | 1.1 | 0.6 | 0.4 | 2.0 | 3.0 | 3.5 | 3.5 | 100.0 |
| DEV05000 | 5.9 | 73.0 | 5.0 | 1.1 | 0.6 | 0.4 | 4.0 | 3.0 | 3.5 | 3.5 | 100.0 |
| DEV05001 | 5.9 | 73.0 | 5.0 | 4.1 | 0.6 | 0.4 | 4.0 | | 3.5 | 3.5 | 100.0 |
| DEV05002 | 2.9 | 73.0 | 5.0 | 4.1 | 0.6 | 0.4 | 4.0 | 3.0 | 3.5 | 3.5 | 100.0 |
| DEV05010 | 6.0 | 71.0 | 5.0 | 3.0 | 0.6 | 0.4 | 4.0 | 3.0 | 3.5 | 3.5 | 100.0 |
| 21011 | 11.0 | 73.0 | 5.0 | 3.0 | 0.6 | 0.4 | | | 3.5 | 3.5 | 100.0 |
| 21012 | 6.0 | 71.0 | 5.0 | 3.0 | 0.6 | 0.4 | 4.0 | 3.0 | 3.5 | 3.5 | 100.0 |

Description of Formulations

DEV04938/DEV04939/DEV04964

Formulations that represent the starting point for development work. DEV04938 is standard high dose of hydrogen peroxide, but strip will be very fast dissolving. DEV04964 is a repeat of DEV04939, and these formulations include both phosphates. DEV04964 and DEV04939 will be as fast dissolving as DEV04938.

DEV04965/DEV04966

These formulations now include both the phosphates and 2 or 4 wt. % of Noveon AA-1. The presence of Noveon is intended to extend dissolution time beyond what would be expected for a high dose non-Noveon containing system. These samples present an improvement in initial disclosure as they now include the phosphates which improve whitening performance of the strips and the Noveon, which extends residence time on teeth.

DEV04969/DEV04970

These formulations now include both the phosphates and 2 or 5 wt. % of hydroxyapatite. The presence of hydroxyapatite is included to reduce severity of dental hypersensitivity (DH) that may occur with use of high-dose hydrogen peroxide whitening products. These samples present an improvement in initial disclosure as they now include the phosphates which improve whitening performance of the strips and the hydroxyapatite, which offers a reduction in DH. The presence of hydroxyapatite at a level of 2 wt. % has no observable effect on dissolution time and the in-vitro dissolution time for DEV04969 strips was found to be only 01:04 (mm:ss).

DEV04971/DEV05000

These formulations include all three additional ingredients (phosphates, Noveon and hydroxyapatite).

DEV05001/DEV05002

DEV05001 contains no hydroxyapatite, but there is an increase in the percentage of peppermint flavour added to this formulation. DEV05002 maintains the higher percentage of flavour, but also reintroduces the hydroxyapatite. A summary of $H_2O_2$ assay results and dissolution times for some of the samples discussed here are presented in Table 9.

TABLE 9

Assay and dissolution times for development samples prepared.

| Sample ID | Weight (mg) | $H_2O_2$ (wt. %) in strip | Weight (mg) | Dissolution time (Hour:Min- utes:Seconds) |
|---|---|---|---|---|
| DEV04969.1 | 108.2 | 8.25 | 117.1 | 00:01:17 |
| DEV04969.2 | 103.6 | 8.55 | 114.4 | 00:01:05 |
| DEV04969.3 | 97.5 | 8.43 | 108.6 | 00:00:56 |
| DEV04969.4 | 113.9 | 7.90 | 98.1 | 00:01:08 |
| DEV04969.5 | 100.7 | 8.43 | 97.8 | 00:00:54 |
| Average | 104.8 | 8.31 | 107.2 | 00:01:04 |

| Sample ID | Weight (mg) | $H_2O_2$ (wt. %) in strip | Weight (mg) | Dissolution time |
|---|---|---|---|---|
| DEV05000.1 | 99.2 | 9.74 | 114.5 | 00:01:34 |
| DEV05000.2 | 99.4 | 9.24 | 111.8 | 00:01:32 |
| DEV05000.3 | 103.7 | 9.10 | 94.8 | 00:01:34 |
| DEV05000.4 | 117.2 | 9.22 | 96.3 | 00:01:30 |
| DEV05000.5 | 96.6 | 9.35 | 94.4 | 00:01:59 |
| Average | 103.2 | 9.33 | 102.4 | 00:01:38 |
| DEV05001.1 | 91.8 | 10.82 | 102.8 | 00:02:51 |
| DEV05001.2 | 98.4 | 10.42 | 96.0 | 00:03:00 |
| DEV05001.3 | 90.0 | 11.08 | 98.3 | 00:02:40 |
| DEV05001.4 | 122.1 | 10.20 | 99.8 | 00:02:49 |
| DEV05001.5 | 93.7 | 10.66 | 120.0 | 00:03:21 |
| Average | 99.2 | 10.63 | 103.4 | 00:02:56 |
| DEV05002.1 | 118.7 | 10.49 | 109.3 | 00:02:45 |
| DEV05002.2 | 98.1 | 10.46 | 93.0 | 00:02:37 |
| DEV05002.3 | 123.4 | 10.64 | 106.2 | 00:02:50 |
| DEV05002.4 | 108.7 | 10.36 | 105.0 | 00:02:51 |
| DEV05002.5 | 90.0 | 10.98 | 97.6 | 00:01:42 |
| Average | 107.8 | 10.59 | 102.2 | 00:02:33 |

Samples that include Noveon have a longer dissolution time than DEV04969 which does not contain Noveon. The longest dissolving Noveon strip (DEV05001) contains 4 wt. % Noveon and 5.9 wt. % of pectin. A reduction in pectin content from 5.9 to 2.9 wt. % sees a slight reduction in dissolution time when the percentage of Noveon is kept constant at 4.0 wt. %.

It can also be observed that the samples which contain Noveon all have relatively high percentages of hydrogen peroxide. These samples demonstrate that it is possible to prepare a dissolving whitening sample that contains phosphates, hydroxyapatite and has an extended dissolution time.

DEV05010

The formulation here reduces slightly the peroxydone percentage (73 to 71 wt. %) and the flavour was reduced to 3 wt. %. The pectin loading was then increased to 6% to hopefully retain the long dissolution time observed in sample DEV05001. Table 10 shows that DEV05010 maintains the high dose of hydrogen peroxide.

TABLE 10

$H_2O_2$ assay results for development sample (DEV05010).

| Sample ID | Weight (mg) | $H_2O_2$ (%) in strip |
|---|---|---|
| DEV05010.1 | 110.0 | 9.99 |
| DEV05010.2 | 130.3 | 10.10 |
| DEV05010.3 | 99.5 | 10.58 |
| DEV05010.4 | 112.4 | 10.12 |
| DEV05010.5 | 118.9 | 10.07 |
| Average | 114.2 | 10.17 |

The 10 wt. % $H_2O_2$ with phosphates development samples manufactured were then taken to pilot manufacture.

Batch 21011

This batch was based on DEV04939 but with a slightly altered loading of flavour. Batch 21011 flavour loading was set at 3.0 wt. % and the level of pectin was reduced to 11.0 wt. %. A single 30 kg batch was prepared and coated. There were no issues encountered during manufacture. Characterisation information from strips of batch 21011 are presented in Table 11 and Table 12.

TABLE 11

$H_2O_2$ assay results of strips from batch 21011.

| Sample ID | Weight (mg) | $H_2O_2$ (%) in strip |
|---|---|---|
| 21011.1 | 125.4 | 9.73 |
| 21011.2 | 122.8 | 9.75 |
| 21011.3 | 124.3 | 9.72 |
| 21011.4 | 122.5 | 9.73 |
| 21011.5 | 122.8 | 9.72 |
| 21011.6 | 121.0 | 9.70 |
| 21011.7 | 121.0 | 9.71 |
| 21011.8 | 124.0 | 9.78 |
| 21011.9 | 121.1 | 9.68 |
| 21011.10 | 123.6 | 9.80 |
| Average | 122.9 | 9.73 |

TABLE 12

Dissolution time for strips from batch 21011.

| Sample | Weight (mg) | Dissolution time |
|---|---|---|
| 21011.1 | 124.3 | 00:01:58 |
| 21011.2 | 124.0 | 00:02:11 |
| 21011.3 | 123.2 | 00:02:34 |
| Average | 123.8 | 00:02:14 |

Batch 21012

This batch was based on DEV05010. A single 30 kg batch was prepared and coated. There were no issues encountered during manufacture. Characterisation information from strips of batch 21012 are presented in Table 13 and Table 14.

TABLE 13

$H_2O_2$ assay results of strips from batch 21012.

| Sample | Weight (mg) | $H_2O_2$ (wt. %) in strip |
|---|---|---|
| 21012.1 | 126.0 | 8.67 |
| 21012.2 | 123.8 | 8.67 |
| 21012.3 | 124.7 | 8.70 |
| 21012.4 | 127.4 | 8.75 |
| 21012.5 | 128.6 | 8.72 |
| 21012.6 | 128.8 | 8.69 |
| 21012.7 | 128.6 | 8.68 |
| 21012.8 | 127.4 | 8.61 |
| 21012.9 | 129.4 | 8.69 |
| 21012.10 | 126.8 | 8.75 |
| Average | 127.2 | 8.69 |

TABLE 14

Dissolution time for strips from batch 21012.

| Sample | Weight (mg) | Dissolution time |
|---|---|---|
| 21012.1 | 126.8 | 00:05:17 |
| 21012.2 | 126.4 | 00:04:31 |
| 21012.3 | 125.1 | 00:04:10 |
| Average | 126.1 | 00:04:39 |

Comparison of 21011 and 21012 and Conclusions

It can be observed that batch 21011 has a higher $H_2O_2$ assay than batch 21012, but the dissolution time is approximately half of the 21012 dissolution time. It is also worth noting that batch 21012 contains hydroxyapatite and Noveon. Both batch 21011 and 21012 contain the blend of phosphates that improve whitening efficacy. These batches indicate that it is possible to commercially manufacture dissolvable whitening strips that contain additional ingredients that can extend dissolution time, improve efficacy, and provide relief from dental hypersensitivity (DH).

Discussion on Dissolution Times

The Dissolution time of dissolvable teeth whitening strips is subjective and there are several factors that can effect dissolution time in the oral cavity such as volume of saliva in the mouth and time since last ingestion of food or drink. Several strips were sampled to volunteers. Each volunteer was asked to record the time required for each strip to dissolve. It is hard to compare dissolution times between volunteers. The average time taken for all strips to dissolve for each user was calculated. The average of the average dissolution times was also calculated to provide an indicative average dissolution time for the strips. This average of averages was used to then compare with the individual dissolution time for each strip. Tables 15 and 16 below shows the results.

TABLE 15

Dissolution Times

| Sample | Dissolution Time (Minutes:Seconds) | | | |
|---|---|---|---|---|
| | V1 | V2 | V3 | Average |
| DEV04938 | 8:19 | 13:40 | 14:26 | 12:08 |
| DEV04939 | 8:12 | 10:45 | 10:03 | 9:40 |
| DEV04965 | 17:21 | 17:30 | 9:58 | 14:56 |
| DEV04966 | 20:31 | 26:20 | 12:30 | 19:47 |
| DEV04970 | 7:14 | 12:30 | 12:48 | 10:51 |
| DEV05000 | 19:55 | 16:20 | 15:46 | 17:20 |
| 21011 | 8:55 | 23:20 | 14:01 | 15:25 |
| 21012 | 27:15 | 36:40 | 18:17 | 27:24 |

TABLE 15-continued

| Dissolution Times | | | | |
|---|---|---|---|---|
| | Dissolution Time (Minutes:Seconds) | | | |
| Sample | V1 | V2 | V3 | Average |
| MAX | 27:15 | 36:40 | 18:17 | |
| MIN | 7:14 | 10:45 | 9:58 | |
| User Average | 14:43 | 19:38 | 13:29 | 15:57 |

TABLE 16

| Compositions of Strips | | | | | | | | | | | |
|---|---|---|---|---|---|---|---|---|---|---|---|
| | Ingredient dry weight (w/w %) | | | | | | | | | | |
| Development number | Pectin | Peroxy-done K-90 | Glycerol | Pepper-mint | Poly-sorbate 80 | Sucralose | Noveon AA1 | Hydroxy-apatite | SHMP | STPP | Total (%) |
| DEV04938 | 12.9 | 80.0 | 5.0 | 1.1 | 0.6 | 0.4 | 0.0 | 0.0 | 0.0 | 0.0 | 100.0 |
| DEV04939 | 12.9 | 72.9 | 5.0 | 1.1 | 0.6 | 0.4 | 0.0 | 0.0 | 3.5 | 3.5 | 100.0 |
| DEV04965 | 10.9 | 73.0 | 5.0 | 1.1 | 0.6 | 0.4 | 2.0 | 0.0 | 3.5 | 3.5 | 100.0 |
| DEV04966 | 8.9 | 73.0 | 5.0 | 1.1 | 0.6 | 0.4 | 4.0 | 0.0 | 3.5 | 3.5 | 100.0 |
| DEV04970 | 9.9 | 71.0 | 5.0 | 1.1 | 0.6 | 0.4 | 0.0 | 5.0 | 3.5 | 3.5 | 100.0 |
| DEV05000 | 5.9 | 73.0 | 5.0 | 1.1 | 0.6 | 0.4 | 4.0 | 3.0 | 3.5 | 3.5 | 100.0 |
| 21011 | 11.0 | 73.0 | 5.0 | 3.0 | 0.6 | 0.4 | | | 3.5 | 3.5 | 100.0 |
| 21012 | 6.0 | 71.0 | 5.0 | 3.0 | 0.6 | 0.4 | 4.0 | 3.0 | 3.5 | 3.5 | 100.0 |

The following conclusions are made from the available data:

Average dissolution time for each user was 15 minutes 57 seconds (15:57).

Three strips had a dissolution time that was longer than the average.

All three strips (DEV04966, DEV05000 and 21012) with longer than average dissolution time contained Noveon AA-1.

Two of the strips (DEV05000 and 21012) contained both Noveon AA-1 and hydroxyapatite.

All strips that contained Noveon AA-1 had longer or comparable average dissolution times than strips that did not.

Longest average dissolution time 27 minutes 24 seconds (27:24) was recorded for 21012 which included both Noveon AA-1 and hydroxyapatite.

Samples that were formulated to have phosphates (DEV04939) and phosphates with hydroxy apatite (DEV04970) had fastest dissolution time. Introduction of Noveon to phosphates and phosphates with hydroxy apatite systems returned dissolution to above average dissolution times.

It is suggested that a dissolution time of between 20-25 minutes should be regarded as extended.

Example 9: In Vitro Whitening Study of 10% Hydrogen Peroxide Dissolving Strip To evaluate the whitening effectiveness of the 10% Hydrogen Peroxide dissolving strip an in vitro whitening study was carried out.

Study Outline

This test was carried out using blocks of bovine enamel that were set into cuvettes using polymethyl acrylate resin. The surfaces of the enamel samples were polished and lightly etched in order to facilitate stain uptake. The samples were then cycled in and out of a staining broth until the colour of the enamel samples reached the darker end of the VITA® Bleachedguide.

The colour parameters (L*, a*, b*) of the stained enamel samples were measured using a calibrated Konica Minolta CM-700d Spectrophotometer. Stained enamel samples with L* values at the lower range of the VITA® Bleachedguide shade range were selected for the study, with six samples assigned each treatment group.

Each stained sample was subjected to 28×30 minute applications of the assigned treatment, with 30 minute immersions in artificial saliva between treatments.

A calibrated CM-700d Spectrophotometer was used to measure the post treatment colour (L*, a*, b*) of the enamel samples after the 1st, 3rd, 7th, 10th, 14th and 28th treatment application.

Delta E is a measure of the total change, with larger delta E values representing increased whitening of the stained enamel surfaces. Prior to this study, the number of delta E units required to move between the shades of the VITA Bleachedguide were calculated. This data was used in this study to convert the total colour change achieved by each treatment (Delta E). The colour (L*, a*, b*) of each tooth shade was measured at four orientations and the mean colour values calculated. The colour of the darkest specimen was used as a reference point for delta E calculations. Delta E for all tooth shades were calculated according to the following equation:

$$\Delta E = \sqrt{((\Delta L^*)^2 + (\Delta a^*)^2 + (\Delta b^*)^2)}$$

Sample Preparation

Blocks of bovine enamel were shaped with a dental abrader then set into cuvettes with polymethacrylate resin. The enamel surfaces were polished with 600 grit silicon carbide paper in order to maintain a standardized enamel surface.

The blocks were etched using the following etching procedure to facilitate stain uptake.

Blocks were immersed in 1% HCl for 1 minute and rinsed.

Blocks were immersed in saturated sodium carbonate for 30 seconds and rinsed.

Blocks were immersed and gently agitated in 1% phytic acid for 1 minute.

Blocks were removed and dabbed dry with absorbent tissue before rinsing with deionised water for approximately 5 minutes.

The blocks were then stored enamel face down on dampened tissue.

Artificial saliva was prepared according to the recipe below in Table 17.

TABLE 17

Recipes for Artificial Saliva

| Ingredient | Molecular Weight | Concentration |
|---|---|---|
| Potassium Chloride | 74.54 | 30 mM |
| Sodium Chloride | 58.44 | 13 mM |
| Potassium Dihydrogen Orthophosphate | 136.09 | 10 mM |
| Calcium Chloride Dihydrate | 147.02 | 3 mM |
| Type II Porcine Stomach Mucin (M2378 Sigma) | NA | 0.22% w/w |
| Sodium Azide as preservative | NA | 0.02% w/w |

A staining solution was prepared that contained tryptone soy broth (TSB), instant tea, instant coffee, mucin type II, ferric chloride, red wine and deionised water. The following instructions were then followed to stain the samples:

The broth was poured into the trough of the staining rig and placed in an incubator at 50° C.

The enamel blocks were attached to the wires of the staining rig.

Blocks were rotated continuously in and out of the staining broth at a speed of approximately 1 rpm such that all blocks were completely submerged at the lowest point of rotation.

Some of the blocks were periodically removed to measure progress of stain uptake (L*).

All blocks were removed once the staining had reached the darker end of the VITA® Bleachedguide.

Treatments

A batch of 10% Hydrogen Peroxide dissolving strips (Lot 20029) was studied in comparison to a batch of Crest 3D Whitestrips (Lot 0050V436) which are non-dissolving, removable strips. Table 18 below shows the Groups.

TABLE 18

Groups and Comparison of Strips

| Group | Product/Treatment Time |
|---|---|
| 1 | Lot: 20029 EXP 2022/09 |
| 2 | Crest 3D WHITESTRIPS ™ (L) 0050V436 |

The formulation of 10 wt. % Hydrogen peroxide Lot 20029 is detailed in Table 19 below.

TABLE 19

Formulation of 10% Hydrogen peroxide Lot 20029

| Ingredient | Dry weight (wt. %) |
|---|---|
| Peroxydone K-90 | 77.4 wt. % |
| Pectin | 10.0 wt. % |
| Glycerol | 5.0 wt. % |
| Noveon AA-1 | 2.0 wt. % |
| Peppermint | 3.5 wt. % |
| Polysorbate 80 | 0.6 wt. % |

TABLE 19-continued

Formulation of 10% Hydrogen peroxide Lot 20029

| Ingredient | Dry weight (wt. %) |
|---|---|
| Stevia | 1.5 wt. % |
| Water | N/A |

Product Treatment

Twenty-eight applications of the assigned treatment (Table 19) were applied to each sample with 30 minute immersions in artificial saliva between each treatment. Samples were immersed in deionised water overnight.

The following treatment procedure was followed for all whitening strips:

Each whitening strip was cut into approximately 1 cm² sections.

The enamel surface of each sample was covered with a drop of artificial saliva.

The whitening strip was applied to the moist enamel surface of the block and left in place for 30 minutes at room temperature. A drop of artificial saliva placed onto the back of whitening strip every five minutes in order to maintain hydration.

After 30 minutes had elapsed, the samples were rinsed with copious amounts of deionised water and gently wiped with a tissue to remove any whitening strip residue.

The samples were then immersed in artificial saliva to ensure each sample remained fully hydrated.

The process was repeated until the end of each working day. Samples were stored overnight in deionised water before re-treatment the following working day. This process was continued until 28 treatments were performed.

Efficacy Assessments

The colour of each block (L*, a*, b*) was measured at baseline and after the 1st, 3rd, 7th, 10th 14th and 28th treatment application. The colour was measured at four orientations using a calibrated Konica Minolta CM-700d chromameter, which generated a mean colour value from four colour measurements.

Results

The mean ΔE change after each of the treatment application is shown in Table 20 below.

TABLE 20

Mean Post Treatment Changes in ΔE

| Treatment | Treatment | ΔE | Standard Deviation |
|---|---|---|---|
| 1$^{st}$ | Crest 3D Whitestrips | 4.89 | 1.10 |
| | Strip 20029 | 2.66 | 1.01 |
| 3$^{rd}$ | Crest 3D Whitestrips | 9.80 | 1.00 |
| | Strip 20029 | 5.20 | 0.89 |
| 7$^{th}$ | Crest 3D Whitestrips | 14.95 | 1.03 |
| | Strip 20029 | 9.09 | 1.37 |
| 10$^{th}$ | Crest 3D Whitestrips | 17.59 | 0.87 |
| | Strip 20029 | 11.02 | 1.52 |
| 14$^{th}$ | Crest 3D Whitestrips | 19.79 | 0.92 |
| | Strip 20029 | 13.44 | 1.53 |
| 28$^{th}$ | Crest 3D Whitestrips | 23.13 | 1.09 |
| | Strip 20029 | 17.70 | 1.73 |

EVALUATION OF RESULTS

Instruction for use of the Crest Whitestrips (Registered Trade Mark) non-dissolving product are that the product is used once per day for 10 days. The dissolving 10 wt. % hydrogen peroxide strip of this invention are intended for up to twice daily usage for up to 14 days. When comparison after 7 and 14 day treatments according to these defined regimens, it can be seen that the whitening of the enamel are statistically equivalent.

Figure 2:
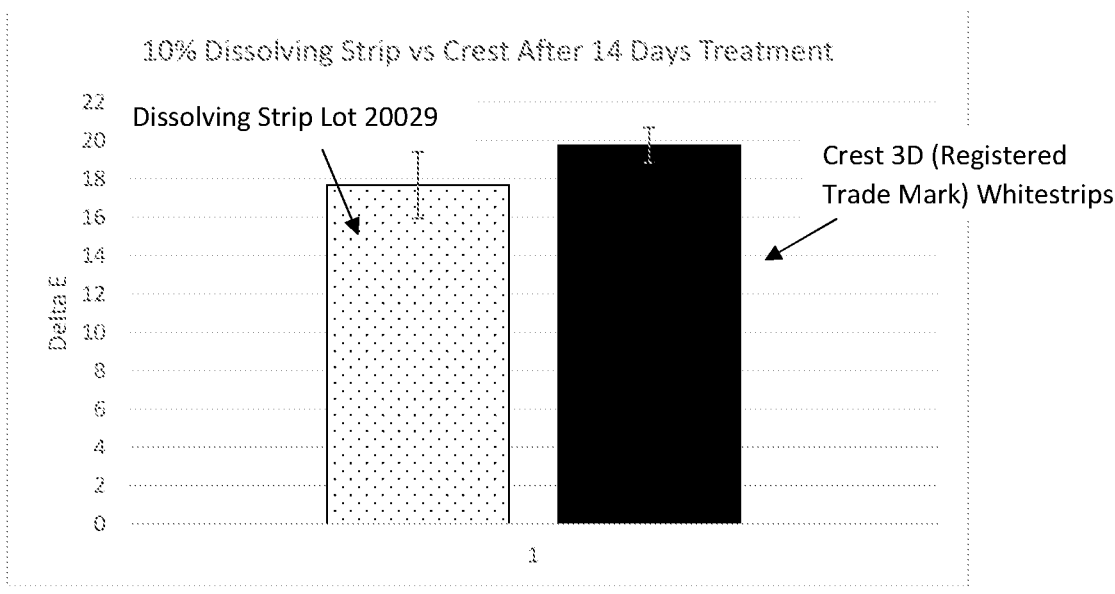
FIG. 2 shows 10 wt. % dissolving strips of Lot 20029 according to the present invention vs. Crest (Registered Trade Mark) according to the prior art after 14 days of treatment.
Figure 3:
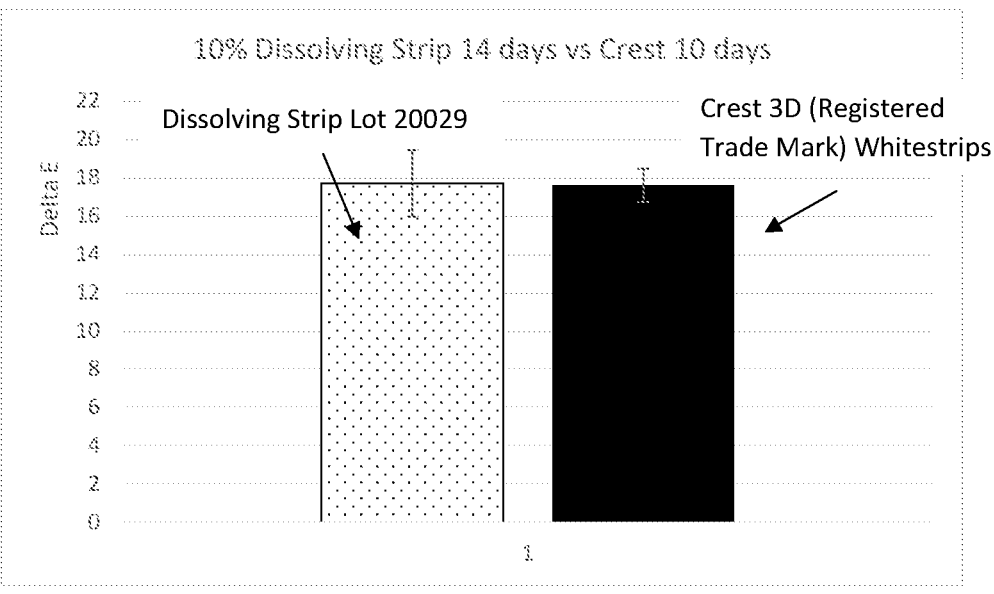
FIG. 3 shows 10 wt. % dissolving strips of Lot 20029 according to the present invention after 14 days vs. Crest (Registered Trade Mark) according to the prior art after 10 days of treatment.

The results are shown in FIGS. 1 to 3.

FIG. 1 shows 10 wt. % dissolving strips of Lot 20029 according to the present invention vs. Crest (Registered Trade Mark) after 7 days of treatment.

FIG. 2 shows 10 wt. % dissolving strips of Lot 20029 according to the present invention vs. Crest (Registered Trade Mark) after 14 days of treatment.

FIG. 3 shows 10 wt. % dissolving strips of Lot 20029 according to the present invention after 14 days vs. Crest (Registered Trade Mark) after 10 days of treatment.

Many modifications and other embodiments of the disclosure will come to mind to one skilled in the art to which this disclosure pertains having the benefit of the teachings presented in the foregoing description; and it will be apparent to those skilled in the art that variations and modifications of the present disclosure can be made without departing from the scope of the appended claims. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A teeth whitening strip or film comprising:

at least one or a combination of polyvinylpyrrolidone (PVP) polymers wherein the amount of the polyvinylpyrrolidone (PVP) polymers is greater than 55 wt. % of the film or strip;

an amount of at least 10 wt. % hydrogen peroxide ($H_2O_2$); and at least one or a combination of polycarbophils in an amount of 1-5 wt. %;

wherein the teeth whitening strip or film dissolves in a person's mouth in 15-30 minutes.

2. A teeth whitening strip or film according to claim 1, wherein the polyvinylpyrrolidone (PVP) is sourced from a complex of PVP and hydrogen peroxide.

3. A teeth whitening strip or film according to claim 1, wherein the polyvinylpyrrolidone (PVP) has a molecular weight of 200,000-5,000,000 Daltons.

4. A teeth whitening strip or film according to claim 1, wherein the polyvinylpyrrolidone (PVP) comprises a polymer complex of 70 wt. % to 90 wt. % PVP and 10 wt. % to 30 wt. % hydrogen peroxide based on the weight of the strip or film.

5. A teeth whitening strip or film according to claim 1, wherein the film or strip is dissolvable or substantially dissolvable in an oral cavity.

6. A teeth whitening strip or film according to claim 1, wherein the teeth whitening strip or film comprises hydrogen peroxide ($H_2O_2$) with the concentration of hydrogen peroxide ($H_2O_2$) of 10 wt. % to 30 wt. % of the strip or film.

7. A teeth whitening strip or film according to claim 1, wherein the amount of polyvinylpyrrolidone (PVP) ranges from 55 wt. % to 99 wt. % of the strip or film.

8. A teeth whitening strip or film according to claim 1, wherein the teeth whitening strip or film comprises the calcium salt of polyacrylic acid cross-linked with divinyl glycol having a viscosity of between 2,000-12,000 cP for a 0.2% solution.

9. A teeth whitening strip or film according to claim 1, wherein the polycarbophil comprises the metal salt of polyacrylic acid cross-linked with a glycol.

10. A teeth whitening strip or film according to claim 1, wherein the polycarbophil comprises the calcium salt of polyacrylic acid cross-linked with divinyl glycol having a viscosity of between 2,000-12,000 cP for a 0.2% solution.

11. A teeth whitening strip or film according to claim 1, wherein the teeth whitening strip or film comprises the polycarbophil in an amount of 2 wt. % to 3 wt. %.

12. A teeth whitening strip or film according to claim 1, wherein the polyvinylpyrrolidone (PVP) polymers form a water soluble, hydrogen bonded complex of linear or substantially linear polymer of n-vinylpyrrolidone (PVP) with a molecular weight of: 100,000-10,000,000 Daltons.

13. A teeth whitening strip or film according to claim 1, wherein the hydrogen peroxide ($H_2O_2$) is complexed with the n-vinylpyrrolidone in a mixture of 1:1 to 1:2 molecular ratios to provide a concentration of hydrogen peroxide 16 wt. % to 20 wt. %.

14. A teeth whitening strip or film according to claim 1, wherein the teeth whitening strips or film may comprise a range of other components including any one of or combination of the following:

one or more polyphosphates;

one or more hydroxyapatites;

one or more water soluble film-forming polymers;

one or more plasticizers; and/or one or more emulsifiers.

15. A teeth whitening strip or film according to claim 1, wherein the film or strip of has a thickness ranging from: 50 μm to 500 μm.

16. A teeth whitening strip or film according to claim 1, wherein the teeth whitening strip or film further comprises a soluble film-forming polymer that is one or more of the group comprising: pullulan; pectin; starch; dextrin; chitosan; alginic acid; salts of alginic acid and/or cellulose derivatives.

17. A teeth whitening strip or film according to claim 1, wherein the teeth whitening strip or film dissolves in a person's mouth in 20-25 minutes.

18. A teeth whitening strip or film according to claim 1, wherein the teeth whitening strip or film has an extended dissolution time.

19. A teeth whitening strip or film according to claim 1, wherein the teeth whitening strip or film further comprises hydroxyapatite (HAP).

20. A teeth whitening strip or film according to claim 1, wherein the teeth whitening strip or film further comprises 2 or 5 wt. % of hydroxyapatite (HAP).

21. A dental kit comprising a tooth whitening strip or film according to claim 1 and a dental aligner.

22. A cosmetic method of bleaching teeth, said cosmetic method comprising at least the step of:

applying a tooth whitening strip or film according to claim 1 on one or more teeth of a subject.

23. A cosmetic method of bleaching teeth, said cosmetic method comprising at least the step of:

applying a tooth whitening strip or film according to claim 1 and a dental aligner on one or more teeth of a subject.

* * * * *